United States Patent
Ofir et al.

(10) Patent No.: US 10,126,829 B2
(45) Date of Patent: Nov. 13, 2018

(54) METHODS AND SYSTEMS FOR MONITORING AND INFLUENCING GESTURE-BASED BEHAVIORS

(71) Applicant: SOMATIX, INC., New York, NY (US)

(72) Inventors: Eran Ofir, Bazra (IL); Uri Schatzberg, Kiryat-Ono (IL)

(73) Assignee: SOMATIX, INC., New York, NY (US)

( * ) Notice: Subject to any disclaimer, the term of this patent is extended or adjusted under 35 U.S.C. 154(b) by 0 days.

(21) Appl. No.: 15/603,246

(22) Filed: May 23, 2017

(65) Prior Publication Data

US 2017/0262064 A1    Sep. 14, 2017

Related U.S. Application Data

(63) Continuation of application No. PCT/US2015/065862, filed on Dec. 15, 2015.
(Continued)

(51) Int. Cl.
*G06F 3/01* (2006.01)
*G06F 3/00* (2006.01)
(Continued)

(52) U.S. Cl.
CPC .............. *G06F 3/017* (2013.01); *A24F 47/00* (2013.01); *A61B 5/00* (2013.01); *A61B 5/11* (2013.01); *A61B 5/1123* (2013.01); *A61B 5/681* (2013.01); *A61B 5/6824* (2013.01); *G06F 3/00* (2013.01); *G06F 3/0346* (2013.01); *A61B 2562/0219* (2013.01); *A61B 2562/0228* (2013.01)

(58) Field of Classification Search
USPC ........................................................ 702/127
See application file for complete search history.

(56) References Cited

U.S. PATENT DOCUMENTS 6,605,038 B1    8/2003    Teller et al.
8,073,707 B2    12/2011    Teller et al.
(Continued)

FOREIGN PATENT DOCUMENTS

CA    2838232 A1    11/2014
FR    3005767 A1    11/2014
(Continued)

OTHER PUBLICATIONS

International search report and written opinion dated Mar. 3, 2016 for PCT Application No. US2015/065862.
(Continued)

*Primary Examiner* — Paul D Lee
(74) *Attorney, Agent, or Firm* — Wilson Sonsini Goodrich & Rosati

(57) ABSTRACT

Methods and systems are provided herein for analyzing, monitoring, and/or influencing a user's behavioral gesture in real-time. A gesture recognition method may be provided. The method may comprise: obtaining sensor data collected using at least one sensor located on a wearable device, wherein said wearable device is configured to be worn by a user; and analyzing the sensor data to determine a probability of the user performing a predefined gesture, wherein the probability is determined based in part on a magnitude of a motion vector in the sensor data, and without comparing the motion vector to one or more physical motion profiles.

28 Claims, 19 Drawing Sheets

Related U.S. Application Data

(60) Provisional application No. 62/092,283, filed on Dec. 16, 2014.

(51) Int. Cl.
*A61B 5/00* (2006.01)
*A61B 5/11* (2006.01)
*A24F 47/00* (2006.01)
*G06F 3/0346* (2013.01)

(56) References Cited

U.S. PATENT DOCUMENTS

| | | |
|---|---|---|
| 8,449,471 B2 | 5/2013 | Tran |
| 8,531,291 B2 | 9/2013 | Tran |
| 8,968,195 B2 | 3/2015 | Tran |
| 9,033,875 B2 | 5/2015 | Teller et al. |
| 9,107,586 B2 | 8/2015 | Tran |
| 9,734,295 B1 | 8/2017 | Movva |
| 9,798,860 B1 | 10/2017 | Movva |
| 2002/0022774 A1 | 2/2002 | Karnieli |
| 2007/0024581 A1* | 2/2007 | Kim .................. G01C 21/16 345/156 |
| 2008/0267444 A1 | 10/2008 | Simons-Nikolova et al. |
| 2009/0012433 A1 | 1/2009 | Fernstrom et al. |
| 2009/0023555 A1 | 1/2009 | Raymond |
| 2009/0062696 A1 | 3/2009 | Nathan et al. |
| 2012/0289244 A1 | 11/2012 | Goyal |
| 2013/0072765 A1 | 3/2013 | Kahn et al. |
| 2013/0190903 A1* | 7/2013 | Balakrishnan ....... A61B 5/7246 700/91 |
| 2013/0194066 A1 | 8/2013 | Rahman et al. |
| 2013/0229508 A1* | 9/2013 | Li .................. G06F 1/3287 348/77 |
| 2014/0018686 A1* | 1/2014 | Medelius ............ A61B 5/7203 600/483 |
| 2014/0139422 A1 | 5/2014 | Mistry et al. |
| 2014/0149754 A1 | 5/2014 | Silva et al. |
| 2014/0191955 A1 | 7/2014 | Raffa et al. |
| 2014/0214448 A1 | 7/2014 | Hanina et al. |
| 2014/0335490 A1 | 11/2014 | Baarman et al. |
| 2014/0347491 A1 | 11/2014 | Connor |
| 2014/0376773 A1* | 12/2014 | Holz .................. G06K 9/00342 382/103 |
| 2015/0078140 A1 | 3/2015 | Riobo et al. |
| 2015/0161516 A1* | 6/2015 | Ghassemzadeh .... G06N 99/005 706/12 |
| 2015/0164377 A1 | 6/2015 | Nathan et al. |
| 2015/0190085 A1 | 7/2015 | Nathan et al. |
| 2015/0254992 A1* | 9/2015 | Sethi ................. G09B 5/06 434/308 |
| 2016/0005299 A1 | 1/2016 | Zomet et al. |
| 2016/0206921 A1 | 7/2016 | Szabados et al. |
| 2017/0220772 A1 | 8/2017 | Vleugels et al. |
| 2017/0293729 A1 | 10/2017 | Movva |

FOREIGN PATENT DOCUMENTS

| | | |
|---|---|---|
| KR | 20140135591 A | 11/2014 |
| WO | WO-2016100368 A1 | 6/2016 |
| WO | WO-2017132690 A1 | 8/2017 |

OTHER PUBLICATIONS

Saleem, et al., Self-Reported Depression, Available at http://clicktherapeutics.com/publications/saleem-2017-society-of-biological-psychiatry.pdf, 1 page, Accessed on Jun. 19, 2017.

Saleheen, et al., PuffMarker: A Multi-Sensor Approach for Pinpointing the Timing of First Lapse in Smoking Cessation, 12 pages.

Clinical Trial of Clickotine, Available at http://clicktherapeutics.com/publications/cns-summit.pdf, 1 page, Accessed on Jun. 19, 2017.

Iacoviello, et al., Clickotine, A Personalized Smartphone App for Smoking Cessation: Initial Evaluation, JMIR Mhealth and Uhealth, 2017, 5(4):e56, 15 pages.

Iacoviello, et al., Six Month Outcomes, Available at http://clicktherapeutics.com/publications/society-for-research-on-nicotine-and-tobacco.pdf, 1 page, Accessed on Jun. 19, 2017.

Novet, Google patents a wearable that tells you to take your medications when you eat, Available at https://venturebeat.com/2016/01/09/google-patents-a-wearable-that-tells-you-to -take-your-medications-when-you-eat/, 17 pages, Accessed on Jun. 19, 2017.

Pai, Researchers use mobile sensors to identify lapses in smoking cessation, stress, Oct. 14, 2015, MobiHealthNews, 2 pages.

International search report dated Apr. 10, 2017 for PCT Application No. US2017-015682.

EP15870892.5 Extended Search Report dated Jun. 14, 2018.

Parate et al. RisQ: Recognizing Smoking Gestures with Inertial Sensors on a Wristband. MobiSys '14, Jun. 16-19, 2014, Bretton Woods, New Hampshire, USA. Copyright 2014 ACM. http://dx.doi.org/10.1145/2594368.2594379.

\* cited by examiner

METHODS AND SYSTEMS FOR MONITORING AND INFLUENCING GESTURE-BASED BEHAVIORS

CROSS-REFERENCE TO RELATED APPLICATION

This application is a continuation of International Application PCT/US2015/065862, filed on Dec. 15, 2015, which application claims priority to U.S. Provisional Application No. 62/092,283 filed on Dec. 16, 2014, the content of which is incorporated herein in its entirety.

BACKGROUND

Recent years have seen the proliferation of wearable devices such as smartwatches and wristbands in the consumer electronics market. Wearable devices make computing technology pervasive by interweaving it into users' daily lives. These wearable devices generally allow users to track their fitness, activities, health and/or well-being, through the use of electronics, software, and sensors in those devices.

Existing wearable devices are typically geared towards improvement of users' fitness and well-being. Additionally, the use of wearable devices can be extended to other areas such as healthcare monitoring. Although wearable devices are capable of collecting large volumes of data about users, there is presently a lack of systems and algorithms that can accurately and efficiently analyze large volumes of data in certain healthcare areas. Examples of those healthcare areas may include monitoring of smoking behavior (e.g., smoking cessation), monitoring of certain types of eating and/or drinking disorders, monitoring of certain types of obsessive compulsive disorders, or monitoring of certain types of neurological diseases that display symptoms associated with repetitive vibration or shaking of a person's hands. Each of the above behaviors may be characterized by different and frequent 'hand-to-mouth' gestures. Existing systems and algorithms often lack the capability to accurately detect and monitor those gestures in real-time.

Thus, there is a need for methods and systems that can accurately detect and monitor various user gestures in real-time, and deliver relevant and personalized information to users in a timely manner to help them manage certain behaviors and habits, thus helping them improve their lives in a step-wise fashion.

SUMMARY

In some conventional systems, a plurality of physical motion profile patterns may be stored in a library, and gesture recognition may be carried out by comparing the user's physical gesture (e.g., a shape of the gesture) against the plurality of motion profile patterns. However, this form of gesture recognition has several shortcomings. For example, body movement is different for different people and depends on a large number of parameters (e.g., body structure and its physical ratios, height, weight, posture (standing/sitting/driving), habits etc.). The body movement for each person may also vary at different times depending on his/her mood and stress level, injuries, location (work/home/at a bar with friends), which hand is being used, time of day, etc. For example, in the case of smoking, people may smoke in different manners, different brands of cigarettes may be smoked differently, and the users' smoking habits may change depending on which hand is being used, their moods, time of day, location etc. A cigarette as used herein may refer to any type of tobacco products including, but not limited to, rolled cigarettes, cigarettes, e-cigarettes, cigars, and/or smoking pipes.

A significantly large number of permutations exist for different types of body movement. To record and store a library of physical motion profile patterns, and compare actual real-time gesture motions of a large number of users to each physical motion profile pattern in the library, would require an immense amount of memory storage and computing power, which most mobile devices and wearable devices currently lack. Additionally, implementation of the above using cloud-based servers may not be feasible in real-time given the high bandwidth required for data communication and processing.

Furthermore, physical motion profile patterns are typically fixed/generalized and do not account for subtle nuances in a user's gesture. As a result, existing gesture recognition systems may not be able to detect whether a user is drinking a hot beverage or a cold beverage, or smoking with a left hand or a right hand. Existing gesture recognition systems also lack adaptability, and are generally unable to capture and reflect changes in the user's gestures and/or behavior over time.

In many instances, people may wish to improve their health and well-being by reducing or eliminating certain types of undesirable behaviors, for example smoking. Smoking is considered a significant risk factor related to cancer and other diseases caused by inhalation of tobacco. Some smokers may embark on smoking cessation programs that are aimed at curing the addiction. However, studies have shown that although about 50% of smokers have tried to quit smoking at some point in time, only 7% of them have successfully managed to do so. Most smokers are susceptible to lapses during the course of those programs, either subconsciously or due to stress, peer pressure, or lack of self-control. In particular, smokers lack tools that can help them to monitor their smoking behavior, and that can proactively provide guidance in real-time during smoking lapses, to encourage them to put out a cigarette and stay on-course with a smoking cessation program.

Additionally, smoking involves unique and complex hand-to-mouth gestures that vary between smokers, depending on the type, size, and/or brand of cigarette, a person's smoking history, gender, day and time of day of smoking, and a plethora of other factors. All these factors make it difficult to track and filter out smoking gestures and patterns.

Accordingly, a need exists for systems and algorithms that can help smokers to control their smoking behaviors, reduce the number of smoked cigarettes, and set goals that are geared towards helping smokers to reduce or quit smoking. In particular, there is a need for systems and algorithms that can accurately recognize hand-to-mouth gestures of a user and detect smoking lapses in real-time. A further need exists to monitor a user's smoking behavior and predict when/ where a user is likely to smoke, so that information (e.g., recommendations) can be provided to help the user stay on course with a smoking cessation program and keep track of program goals. Such information may be personalized and dynamically provided in real-time to the user on a computing device. The information can help the user to make informed decisions about his/her overall well-being, and show the user the progress that has been made. The systems and methods disclosed herein address at least the above needs.

Embodiment #1

A gesture recognition method may comprise: obtaining sensor data collected using at least one sensor located on a wearable device, wherein said wearable device is configured to be worn by a user; and analyzing the sensor data to determine a probability of the user performing a predefined gesture, wherein the probability is determined based in part on a magnitude of a motion vector in the sensor data, and without comparing the motion vector to one or more physical motion profiles.

Embodiment #2

A system for implementing gesture recognition may comprise a memory for storing sensor data collected using at least one sensor located on a wearable device, wherein the wearable device is configured to be worn by a user. The system may further comprise one or more processors configured to execute the set of software instructions to: analyze the sensor data to determine a probability of the user performing a predefined gesture, wherein the probability is determined based in part on a magnitude of a motion vector in the sensor data, and without comparing the motion vector to one or more physical motion profiles.

Embodiment #3

A tangible computer readable medium storing instructions that, when executed by one or more processors, causes the one or more processors to perform a computer-implemented gesture recognition method, may be provided. The method may comprise: obtaining sensor data collected using at least one sensor located on a wearable device, wherein said wearable device is configured to be worn by a user; and analyzing the sensor data to determine a probability of the user performing a predefined gesture, wherein the probability is determined based in part on a magnitude of a motion vector in the sensor data, and without comparing the motion vector to one or more physical motion profiles.

In one or more of above embodiments #1, #2, and/or #3, the predefined gesture may be selected from a group of different gestures associated with different activities. The gestures associated with the different activities may be differentiated from one another based at least on the magnitude of different motion vectors in the sensor data, and without comparing the motion vectors to the one or more physical motion profiles. The at least one sensor may comprise an accelerometer and a gyroscope.

The magnitude of the motion vector may comprise: (1) a magnitude of the acceleration vector obtained from the accelerometer, and/or (2) a magnitude of an angular velocity vector obtained from the gyroscope. The probability may be determined based in part on the magnitude of the acceleration vector and/or the magnitude of the angular velocity vector. The probability may be determined based in part on the magnitude of the acceleration vector and/or the magnitude of the angular velocity vector within different temporal periods, and without comparing the acceleration vector and/or the angular velocity vector to the one or more physical motion profiles.

A pitch angle, a roll angle, and/or a yaw angle of the wearable device may be calculated based on the acceleration vector and/or the angular velocity vector. The probability may be determined based on the pitch angle, the roll angle, and/or the yaw angle.

A correlation may be determined between the magnitude of the acceleration vector and the magnitude of the angular velocity vector within different temporal periods, so as to determine the probability of the user performing the predefined gesture.

At least one sensor may further comprise one or more of the following: a magnetometer, a heart rate monitor, a global positioning system (GPS) receiver, an external temperature sensor, a microphone, a skin temperature sensor, a capacitive sensor, and/or a sensor configured to detect a galvanic skin response.

The sensor data may be analyzed without comparing the sensor data against the one or more physical motion profiles. A shape of the one or more physical motion profiles may be substantially similar to a shape of one or more physical gestures of the user.

Analyzing the sensor data may further comprise calculating a multi-dimensional distribution function, wherein said multi-dimensional distribution function is a probability function of a plurality of features. The plurality of features may be associated with various aspects of the predefined gesture. The plurality of features may comprise two or more of the following features: (1) a time duration of a submotion during the gesture; (2) the magnitude of the acceleration vector; (3) the magnitude of the angular velocity vector; (4) the roll angle; and (5) the pitch angle. The multi-dimensional distribution function may be associated with one or more characteristic of the predefined gesture. The plurality of features may be encoded within the sensor data, and extracted from the sensor data. Two or more features may be correlated.

The multi-dimensional distribution function may be configured to return a single probability value between 0 and 1, and wherein the probability value represents a probability of each feature. In some cases, each feature may be represented by a discrete value. In other cases, each feature may be measurable along a continuum. The multi-dimensional distribution function may be calculated by using Singular Value Decomposition (SVD) to de-correlate the two or more correlated features such that they are approximately orthogonal to each other. The use of the SVD may reduce a processing time required to compute the probability value for the multi-dimensional distribution function and may reduce the amount of sensor data needed to determine the probability of the user performing the predefined gesture. The multi-dimensional distribution function may be calculated by multiplying the de-correlated (rotated) 1D probably density distribution of each feature, such that the multi-dimensional distribution function $f(p_1, p_2, \ldots, p_n) = f(p_1) * f(p_2) * \ldots * f(p_n)$. The function $f(p_1)$ may be a 1D probability density distribution of a first feature, the function $f(p_2)$ may be a 1D probability density distribution of a second feature, and the function $f(p_n)$ may be a 1D probability density distribution of a n-th feature. The 1D probability density distribution of each feature may be obtained from a sample size of each feature. In some cases, the sample size may be constant across all of the features. In other cases, the sample size may be variable between different features. One or more of the plurality of features may be determined whether they are statistically insignificant. The one or more statistically insignificant features may have low correlation with the predefined gesture. The one or more statistically insignificant features may be removed from the multi-dimensional distribution function. Removing the one or more statistically insignificant features from the multi-dimensional distribution function may reduce a computing time and/or power required to calculate the probability value for the multi-dimensional distribution function.

Analyzing the sensor data may further comprise applying a filter to the sensor data. The filter may be a higher order complex filter comprising a finite-impulse-response (FIR) filter and/or an infinite-impulse-response (IIR) filter. The filter may be a Kalman filter or a Parks-McClellan filter.

The wearable device may be configured to transmit the sensor data to a user device and/or a server for the analysis of the sensor data. The transmission of the sensor data may be via one or more wireless or wired communication channels. The one or more wireless communication channels may comprise BLE (Bluetooth Low Energy), WiFi, 3G, and/or 4G networks.

The sensor data may be stored in a memory on the wearable device when the wearable device is not in operable communication with the user device and/or the server. The sensor data may be transmitted from the wearable device to the user device and/or the server when operable communication between the wearable device and the user device and/or the server is re-established.

A data compression step may be applied to the sensor data. The compression of the sensor data may reduce a bandwidth required to transmit the sensor data, and the compression of the sensor data may reduce a power consumption of the wearable device during the transmission of the sensor data. The data compression step may comprise calculating a time-based difference between samples of the sensor data along different axes of measurement. The time-based difference may be transmitted from the wearable device to a user device and/or a server. The sensor data may be compressed using a predefined number of bits.

The one or more sensors may be configured to collect the sensor data at a predetermined frequency. The predetermined frequency may be configured to optimize and/or reduce a power consumption of the wearable device. The predetermined frequency may range from about 10 Hz to about 20 Hz. The one or more sensors may be configured to collect the sensor data at a first predetermined frequency when the probability that the user is performing the gesture is below a predefined threshold value. The one or more sensors may be configured to collect the sensor data at a second predetermined frequency when the probability that the user is performing the gesture is above a predefined threshold value. The second predetermined frequency may be higher than the first predetermined frequency. The one or more sensors may be configured to collect the sensor data for a predetermined time duration. The one or more sensors may be configured to collect the sensor data continuously in real-time when the wearable device is powered on.

The one or more sensors may comprise a first group of sensors and a second group of sensors. The first group of sensors and the second group of sensors may be selectively activated to reduce power consumption of the wearable device. The first group of sensors and the second group of sensors may be selectively activated to reduce an amount of the collected sensor data. The reduction in the amount of sensor data may allow for faster analysis/processing of the sensor data, and reduce an amount of memory required to store the sensor data. The first group of sensors may be activated when the wearable device is powered on. The first group of sensors may be used to determine the probability of the user performing the predefined gesture. The second group of sensors may be inactive when the probability that the user is performing the gesture is below a predefined threshold value. The second group of sensors may be selectively activated when the wearable device is powered on and when the probability that the user is performing the gesture is above a predefined threshold value. The second group of sensors may be selectively activated upon determining that the user is performing the predefined gesture. The second group of sensors may be activated to collect additional sensor data, so as to confirm that the user is performing the predefined gesture, monitor the gesture, and collect additional sensor data relating to the gesture.

The wearable device may be configured to operate in a plurality of energy and/or performance modes. The plurality of modes may comprise a low power mode in which at least an accelerometer in the wearable device is turned on. The wearable device may have low power consumption when the wearable device is in the low power mode. An accuracy of detection of the predefined gesture may be reduced when the wearable device is in the low power mode, since less information (less amount of sensor data) is available for analysis in the low power mode. The plurality of modes may comprise an accuracy mode in which all of the sensors are turned on. The wearable device may have high power consumption when the wearable device is in the accuracy mode. An accuracy of detection of the predefined gesture may be improved when the wearable device is in the accuracy mode, since more information (greater amount of sensor data) is available for analysis in the accuracy mode. In some cases, the sensor data may not be analyzed or transmitted when the wearable device is in an idle mode or a charging mode.

The sensor data may comprise at least one of the following parameters: (1) an active hand which the user uses to make the gesture; (2) a pulse pattern of the user; (3) a location of the user; (4) identifiers of the wearable device and/or a user device; and (5) behavioral statistics of the user relating to the gesture. An identity of the user may be authenticated based on the one or more of the parameters. The probability of the user performing the predefined gesture at different times of the day and/or at different geographical locations may be determined. A frequency of the sensor data collection may be adjusted based on the different times of the day and/or the different geographical locations. The frequency of the sensor data collection may be increased at times of the day and/or at geographical locations where the probability of the user performing the predefined gesture is above a predetermined threshold value. The frequency of the sensor data collection may be reduced at times of the day and/or at geographical locations where the probability of the user performing the predefined gesture is below a predetermined threshold value. One or more of the sensors may be selectively activated based on the probability of the user performing the predefined gesture at different times of the day and/or at different geographical locations.

Embodiment #4

A method of detecting a smoking gesture may comprise: obtaining sensor data collected using one or more sensors, wherein said sensors comprise a multi-axis accelerometer that is located on a wearable device configured to be worn by a user; and analyzing the sensor data to determine a probability of the user smoking, wherein the probability is determined based in part on a magnitude of an acceleration vector in the sensor data, and without comparing the motion vector to one or more physical motion profiles.

Embodiment #5

A system for implementing gesture recognition may comprise a memory for storing sensor data collected using one or more sensors, wherein the sensors may comprise a multi-axis accelerometer that is located on a wearable device configured to be worn by a user. The system may further comprise one or more processors configured to execute a set of software instructions to: analyze the sensor data to determine a probability of the user smoking, wherein the probability is determined based in part on a magnitude of an acceleration vector in the sensor data, and without comparing the motion vector to one or more physical motion profiles.

Embodiment #6

A tangible computer readable medium storing instructions that, when executed by one or more processors, causes the one or more processors to perform a computer-implemented gesture recognition method, may be provided. The method may comprise: obtaining sensor data collected using one or more sensors, wherein said sensors comprise a multi-axis accelerometer that is located on a wearable device configured to be worn by a user; and analyzing the sensor data to determine a probability of the user smoking, wherein the probability is determined based in part on a magnitude of an acceleration vector in the sensor data, and without comparing the motion vector to one or more physical motion profiles.

In one or more of above embodiments #4, #5, and/or #6, analyzing the sensor data may comprise analyzing one or more features in the sensor data to determine a probability of the user taking a cigarette puff. The features may comprise at least one of the following: (1) a time duration that a potential cigarette is detected in the user's mouth; (2) a roll angle of the user's arm; (3) a pitch angle of the smoker's arm; (4) a time duration of a potential smoking puff; (5) a time duration between consecutive potential puffs; (6) number of potential puffs that the user takes to finish smoking a cigarette; (7) the magnitude of the acceleration vector; (8) a speed of the user's arm; (9) an inhale region corresponding to an arm-to-mouth gesture; and/or (10) an exhale region corresponding to an arm-down-from-mouth gesture. The features may be extracted from the sensor data.

The probability of the user smoking may be adjusted based on one or more user inputs. The user inputs may comprise: (1) an input signal indicating that the user did not smoke; (2) an input signal indicating that the user had smoked; and (3) an input signal indicating that the user had smoked but the smoking gesture was not recognized or detected. A user configuration file (UCF) for the user may be generated based on the analyzed sensor data and the one or more user inputs. The UCF may be general to a plurality of users. The UCF may become unique to each user after a period of time. The UCF may be configured to adapt and change over time depending on the user's behavior. The UCF may comprise a list of user parameters associated with different activities besides smoking. The different activities may comprise at least one of the following: standing, walking, sitting, driving, drinking, eating, and/or leaning while standing or sitting. The UCF may be dynamically changed when no smoking of the user has been detected for a predetermined time period. The UCF may be dynamically changed to verify that the user has not smoked for the predetermined time period.

The user may be determined whether to be smoking with a right hand or a left hand based on a roll angle, a pitch angle, and/or a yaw angle extracted from the sensor data. The UCF may be updated with the left/right hand information of the user.

The probability may be determined using a multi-dimensional distribution function that is associated with one or more smoking characteristics. The one or more smoking characteristics may comprise the user taking one or more cigarette puffs. The multi-dimensional distribution function may be generated for each puff The probability of the user smoking may be determined based on: (1) a number of potential puffs; (2) the multi-dimensional distribution function for each potential puff; and (3) a time duration in which the number of potential puffs occur. A sum of the multi-dimensional distribution functions for a number of potential puffs may be determined whether to be equal to or greater than a predetermined probability threshold. The user may be determined to be smoking when the sum is equal to or greater than the predetermined probability threshold, and the user may be determined not to be smoking when the sum is less than the predetermined probability threshold. The user may be determined to be smoking when a predetermined number of puffs have been detected within a predetermined time period. The roll and pitch angles associated with the potential puffs may be analyzed, and the puffs whose roll and pitch angles fall outside of a predetermined roll/pitch threshold may be discarded. A time duration between the potential puffs may be analyzed, and the puffs where the time duration falls outside of a predetermined time period may be discarded.

The probability of the user smoking at different times of the day and/or at different geographical locations may be determined. A frequency of the sensor data collection may be adjusted based on the different times of the day and/or the different geographical locations. The frequency of the sensor data collection may be increased at times of the day and/or at geographical locations where the probability of the user smoking is above a predetermined threshold value. The frequency of the sensor data collection may be reduced at times of the day and/or at geographical locations where the probability of the user smoking is below a predetermined threshold value. One or more of the sensors may be selectively activated based on the probability of the user smoking at different times of the day and/or at different geographical locations.

It shall be understood that different aspects of the disclosure can be appreciated individually, collectively, or in combination with each other. Various aspects of the disclosure described herein may be applied to any of the particular applications set forth below or for any other types of energy monitoring systems and methods.

Other objects and features of the present disclosure will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Reference will now be made in detail to some exemplary embodiments of the disclosure, examples of which are illustrated in the accompanying drawings. Wherever possible, the same reference numbers will be used throughout the drawings and disclosure to refer to the same or like parts.

Introduction

Wearable devices have become increasingly popular in recent years. Although wearable devices are capable of collecting large volumes of data about users, there is presently a lack of systems and algorithms that can accurately and efficiently analyze large volumes of data, particularly in certain healthcare areas.

The embodiments of the disclosure described herein can enable real-time measurement of hand-to-mouth gestures applicable to certain healthcare areas (e.g., monitoring of smoking behavior for smoking cessation, etc.). The data can be used to help users effectively manage or control their behavior/habits. In some cases, the data may be used by healthcare organizations or insurance companies to tailor preventive behavioral health programs for users, that can help users to improve their health and well-being.

Embodiments of the disclosure can help users to better understand their behaviors/habits in order to more effectively change their behaviors/habits. For example, in the case of smoking, certain embodiments of the disclosure allow users to see the number of cigarettes smoked by time and location, number of puffs, the social context in which smoking occurred, etc. Smoking statistics and alerts can be generated for different users, and goals may be set for cessation programs. A user can also compare his progress in a smoking cessation program to other users in a same social network. In some cases, incentives may be provided to users in real-time to reward progress and to further motivate the user.

Next, various embodiments of the disclosure will be described with reference to the drawings.

Figure 1:
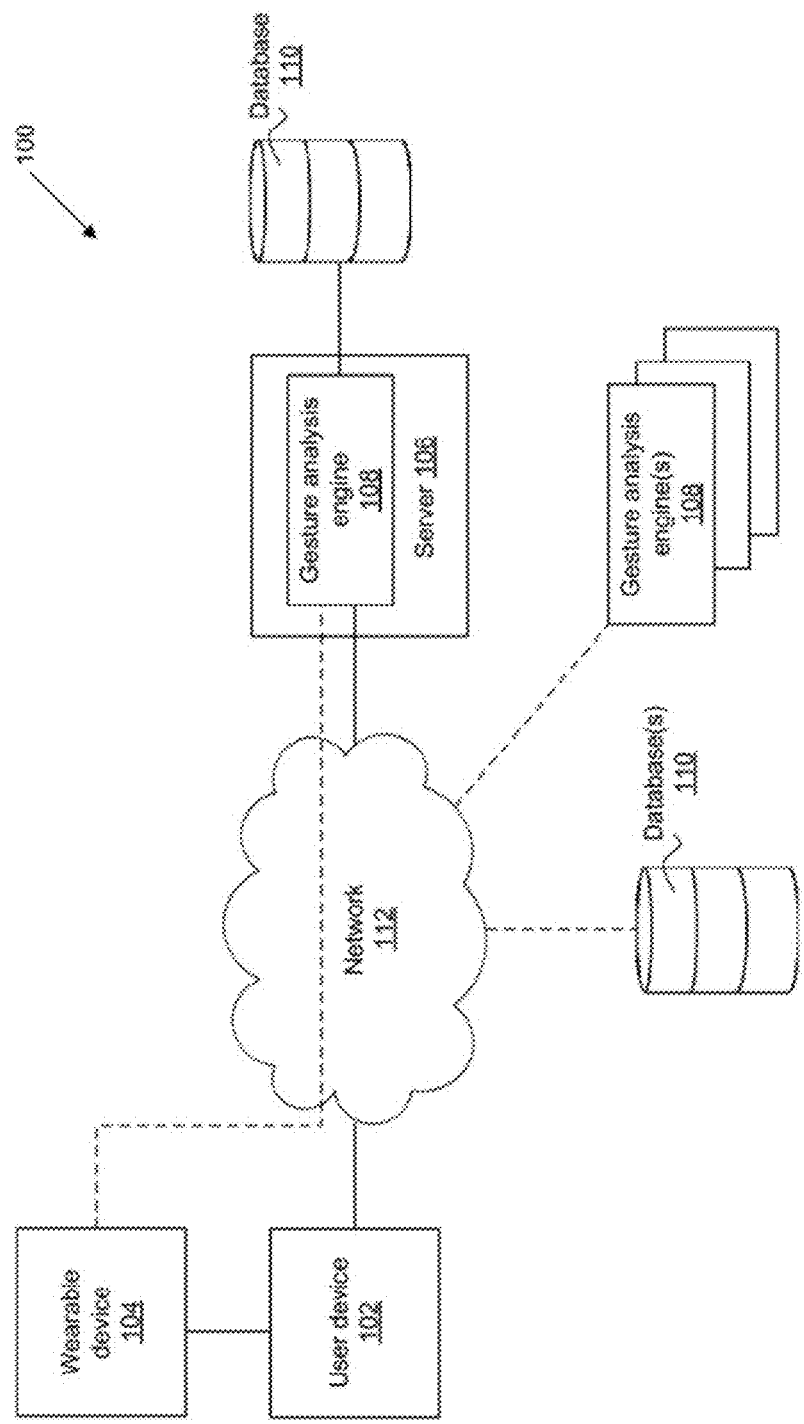
FIG. 1 illustrates a healthcare monitoring system in accordance with some embodiments.

FIG. 1 illustrates a healthcare monitoring system in accordance with some embodiments. In one aspect, a healthcare monitoring system 100 may include a user device 102, a wearable device 104, a server 106, a gesture analysis engine 108, and a database 110. Each of the components 102, 104, 106, 108, and 110 may be operatively connected to one another via network 112 or any type of communication links that allows transmission of data from one component to another. The gesture analysis engine may be configured to analyze input data from the user device and/or wearable device in order to detect and/or monitor a predetermined gesture, and to provide information (e.g., recommendations) to assist a user in managing behavior associated with the predetermined gesture. The gesture analysis engine may be implemented anywhere within the healthcare monitoring system, and/or outside of the healthcare monitoring system. In some embodiments, the gesture analysis engine may be implemented on the server. In other embodiments, the gesture analysis engine may be implemented on the user device. Additionally, the gesture analysis engine may be implemented on the wearable device. In some further embodiments, a plurality of gesture analysis engines may be implemented on one or more servers, user devices, and/or wearable devices. Alternatively, the gesture analysis engine may be implemented in one or more databases. The gesture analysis engine may be implemented using software, hardware, or a combination of software and hardware in one or more of the above-mentioned components within the healthcare monitoring system.

User device 102 may be a computing device configured to perform one or more operations consistent with the disclosed embodiments. Examples of user devices may include, but are not limited to, mobile devices, smartphones/cellphones, tablets, personal digital assistants (PDAs), laptop or notebook computers, desktop computers, media content players, television sets, video gaming station/system, virtual reality systems, augmented reality systems, microphones, or any electronic device capable of analyzing, receiving, providing or displaying certain types of behavioral data (e.g., smoking data) to a user. The user device may be a handheld object. The user device may be portable. The user device may be carried by a human user. In some cases, the user device may be located remotely from a human user, and the user can control the user device using wireless and/or wired communications.

User device 102 may include one or more processors that are capable of executing non-transitory computer readable media that may provide instructions for one or more operations consistent with the disclosed embodiments. The user device may include one or more memory storage devices comprising non-transitory computer readable media including code, logic, or instructions for performing the one or more operations. The user device may include software applications that allow the user device to communicate with and transfer data between wearable device 104, server 106, gesture analysis engine 108, and/or database 110. The user device may include a communication unit, which may permit the communications with one or more other components in healthcare monitoring system 100. In some instances, the communication unit may include a single communication module, or multiple communication modules. In some instances, the user device may be capable of interacting with one or more components in healthcare monitoring system 100 using a single communication link or multiple different types of communication links.

User device 102 may include a display. The display may be a screen. The display may or may not be a touchscreen. The display may be a light-emitting diode (LED) screen, OLED screen, liquid crystal display (LCD) screen, plasma screen, or any other type of screen. The display may be configured to show a user interface (UI) or a graphical user interface (GUI) rendered through an application (e.g., via an application programming interface (API) executed on the user device). The GUI may show images that permit a user to monitor one or more types of behavior (e.g., smoking). The user device may also be configured to display webpages and/or websites on the Internet. One or more of the webpages/websites may be hosted by server 106 and/or rendered by gesture analysis engine 108.

A user may navigate within the GUI through the application. For example, the user may select a link by directly touching the screen (e.g., touchscreen). The user may touch any portion of the screen by touching a point on the screen. Alternatively, the user may select a portion of an image with aid of a user interactive device (e.g., mouse, joystick, keyboard, trackball, touchpad, button, verbal commands, gesture-recognition, attitude sensor, thermal sensor, touch-capacitive sensors, or any other device). A touchscreen may be configured to detect location of the user's touch, length of touch, pressure of touch, and/or touch motion, whereby each of the aforementioned manner of touch may be indicative of a specific input command from the user.

Wearable device 104 may include smartwatches, wristbands, glasses, gloves, headgear (such as hats, helmets, virtual reality headsets, augmented reality headsets, head-mounted devices (HMD), headbands), pendants, armbands, leg bands, shoes, vests, motion sensing devices, etc. The wearable device may be configured to be worn on a part of a user's body (e.g., a smartwatch or wristband may be worn on the user's wrist). The wearable device may include one or more types of sensors. Examples of types of sensors may include inertial sensors (e.g., accelerometers, gyroscopes, and/or gravity detection sensors, which may form inertial measurement units (IMUs)), location sensors (e.g., global positioning system (GPS) sensors, mobile device transmitters enabling location triangulation), heart rate monitors, external temperature sensors, skin temperature sensors, capacitive touch sensors, sensors configured to detect a galvanic skin response (GSR), vision sensors (e.g., imaging devices capable of detecting visible, infrared, or ultraviolet light, such as cameras), proximity or range sensors (e.g., ultrasonic sensors, lidar, time-of-flight or depth cameras), altitude sensors, attitude sensors (e.g., compasses), pressure sensors (e.g., barometers), humidity sensors, vibration sensors, audio sensors (e.g., microphones), and/or field sensors (e.g., magnetometers, electromagnetic sensors, radio sensors).

Wearable device 104 may further include one or more devices capable of emitting a signal into an environment. For instance, the wearable device may include an emitter along an electromagnetic spectrum (e.g., visible light emitter, ultraviolet emitter, infrared emitter). The wearable device may include a laser or any other type of electromagnetic emitter. The wearable device may emit one or more vibrations, such as ultrasonic signals. The wearable device may emit audible sounds (e.g., from a speaker). The wearable device may emit wireless signals, such as radio signals or other types of signals.

Any examples herein of sensors that may be present in wearable device 104 may also apply to user device 102. For instance, one or more different sensors may be incorporated into user device 102.

Although FIG. 1 illustrates user device 102 and wearable device 104 as two separate devices, the disclosure is not limited thereto. In some embodiments, the user device and the wearable device may be integrated into a single device. In some embodiments, the wearable device may be incorporated into the user device. In other embodiments, the user device may be incorporated into the wearable device. Alternatively, the user device may be capable of performing one or more functions of the wearable device. Optionally, the wearable device may be capable of performing one or more functions of the user device, and the user device may be capable of performing one or more functions of the wearable device.

User device 102 and wearable device 104 may be operated by one or more users consistent with the disclosed embodiments. In some embodiments, a user may be associated with a unique user device and a unique wearable device. Alternatively, a user may be associated with a plurality of user devices and wearable devices. A user as described herein may refer to an individual or a group of individuals who are seeking to improve their well-being through healthcare monitoring system 100. For example, a smoker or a group of smokers may desire to quit smoking. A person or a group of persons suffering from alcoholism may desire to quit drinking. A person or a group of persons suffering from an excessive eating disorder may desire to reduce their food intake. The above users can use healthcare monitoring system 100 to control and manage those behaviors.

A user may be registered or associated with an entity that provides services associated with one or more operations performed by the disclosed embodiments. For example, a user may be a registered user of an entity (e.g., a company, an organization, an individual, etc.) that provides gesture analysis engine 108 to perform operations for assisting the user in managing certain types of behaviors (e.g., smoking). The disclosed embodiments are not limited to any specific relationships or affiliations between user(s) of user device 102 and wearable device 104, and an entity, person(s), or entities that provides gesture analysis engine 108.

User device 102 and/or wearable device 104 may be configured to receive input from one or more users. A user may provide an input to the user device and/or wearable device using an input device, for example, a keyboard, a mouse, a touch-screen panel, voice recognition and/or dictation software, or any combination of the above. The user input may include statements, comments, questions, or answers relating to certain types of behavior (e.g., smoking). Different users may provide different inputs. For example, a user may provide an input to indicate whether the use is smoking or had smoked within a predetermined time period. In some instances, the input may also indicate how the user is feeling (e.g., whether the user is feeling motivated or discouraged) during the course of a program aimed at mitigating certain behaviors (e.g., smoking). In those instances, the user's input may be indicative of the user's thoughts, feelings, moods, opinions, questions, and/or answers relating to smoking.

Server 106 may be one or more server computers configured to perform one or more operations consistent with the disclosed embodiments. In one aspect, the server may be implemented as a single computer, through which user device 102 and wearable device 104 are able to communicate with gesture analysis engine 108 and database 110. In some embodiments, the user device and/or the wearable device may communicate with the gesture analysis engine directly through the network. In some embodiments, the server may communicate on behalf of the user device and/or the wearable device with the gesture analysis engine or database through the network. In some embodiments, the server may embody the functionality of one or more of gesture analysis engines. In some embodiments, one or more gesture analysis engines may be implemented inside and/or outside of the server. For example, the gesture analysis engines may be software and/or hardware components included with the server or remote from the server.

In some embodiments, the user device and/or the wearable device may be directly connected to the server through a separate link (not shown in FIG. 1). In certain embodiments, the server may be configured to operate as a front-end device configured to provide access to one or more gesture analysis engines consistent with certain disclosed embodiments. The server may, in some embodiments, utilize one or more gesture analysis engines to analyze input data from the user device and/or wearable device in order to detect and/or monitor a predetermined gesture, and to provide information (e.g., recommendations) to assist the user in managing behavior associated with the predetermined gesture. The server may also be configured to store, search, retrieve, and/or analyze data and information stored in one or more of the databases. The data and information may include raw data collected from accelerometers and gyroscopes on one or more wearable devices, as well as each user's historical behavioral pattern and social interactions relating to the type of behavior (e.g., smoking). While FIG. 1 illustrates the server as a single server, in some embodiments, multiple devices may implement the functionality associated with a server.

A server may include a web server, an enterprise server, or any other type of computer server, and can be computer programmed to accept requests (e.g., HTTP, or other protocols that can initiate data transmission) from a computing device (e.g., user device and/or wearable device) and to serve the computing device with requested data. In addition, a server can be a broadcasting facility, such as free-to-air, cable, satellite, and other broadcasting facility, for distributing data. A server may also be a server in a data network (e.g., a cloud computing network).

A server may include known computing components, such as one or more processors, one or more memory devices storing software instructions executed by the processor(s), and data. A server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods can be implemented in hardware components or combinations of hardware and software such as, for example, ASICs, special purpose computers, or general purpose computers.

While FIG. 1 illustrates the server as a single server, in some embodiments, multiple devices may implement the functionality associated with server.

Network 112 may be a network that is configured to provide communication between the various components illustrated in FIG. 1. The network may be implemented, in some embodiments, as one or more networks that connect devices and/or components in the network layout for allowing communication between them. For example, user device 102, wearable device 104, and gesture analysis engine 108 may be in operable communication with one another over network 112. Direct communications may be provided between two or more of the above components. The direct communications may occur without requiring any intermediary device or network. Indirect communications may be provided between two or more of the above components. The indirect communications may occur with aid of one or more intermediary device or network. For instance, indirect communications may utilize a telecommunications network. Indirect communications may be performed with aid of one or more router, communication tower, satellite, or any other intermediary device or network. Examples of types of communications may include, but are not limited to: communications via the Internet, Local Area Networks (LANs), Wide Area Networks (WANs), Bluetooth, Near Field Communication (NFC) technologies, networks based on mobile data protocols such as General Packet Radio Services (GPRS), GSM, Enhanced Data GSM Environment (EDGE), 3G, 4G, or Long Term Evolution (LTE) protocols, Infra-Red (IR) communication technologies, and/or Wi-Fi, and may be wireless, wired, or a combination thereof. In some embodiments, the network may be implemented using cell and/or pager networks, satellite, licensed radio, or a combination of licensed and unlicensed radio. The network may be wireless, wired, or a combination thereof.

User device 102, wearable device 104, server 106, and/or gesture analysis engine 110 may be connected or interconnected to one or more databases 110. The databases may be one or more memory devices configured to store data. Additionally, the databases may also, in some embodiments, be implemented as a computer system with a storage device. In one aspect, the databases may be used by components of the network layout to perform one or more operations consistent with the disclosed embodiments.

In one embodiment, the databases may comprise storage containing a variety of data sets consistent with disclosed embodiments. For example, the databases may include, for example, raw data collected by accelerometers and gyroscopes located on wearable device 104. The databases may also include users' preferences, historical behavioral patterns, traits associated with a type of behavior, changes and/or improvements in the users' lifestyles, the users' success at managing or overcoming certain types of behaviors, the users' social interaction relating to a certain type of behavior, statements or comments indicative of how the user is feeling at different points in time, etc. In some embodiments, the database(s) may include crowd-sourced data comprising comments and insights relating to user's attempts to quit smoking obtained from internet forums and social media websites. The Internet forums and social media websites may include personal and/or group blogs, Facebook™, Twitter™, etc. Additionally, in some embodiments, the database(s) may include crowd-sourced data comprising comments and insights relating to other users' attempts to quit smoking, whereby those comments and insights may be directly input by one or more other users into the gesture analysis engine(s). The crowd-sourced data may contain up-to-date or current information on the progress of other users in trying to quit smoking, recommendations on ways to quit smoking, etc. The crowd-sourced data may be provided by other users who have experience with trying to quit smoking, or who have successfully managed to quit smoking.

In certain embodiments, one or more of the databases may be co-located with the server, may be co-located with one another on the network, or may be located separately from other devices (signified by the dashed line connecting the database(s) to the network). One of ordinary skill will recognize that the disclosed embodiments are not limited to the configuration and/or arrangement of the database(s).

Any of the user device, wearable device, server, gesture analysis engine, and the database may, in some embodiments, be implemented as a computer system. Additionally, while the network is shown in FIG. 1 as a "central" point for communications between components, the disclosed embodiments are not so limited. For example, one or more components of the network layout may be interconnected in a variety of ways, and may in some embodiments be directly connected to, co-located with, or remote from one another, as one of ordinary skill will appreciate. Additionally, while some disclosed embodiments may be implemented on the server, the disclosed embodiments are not so limited. For instance, in some embodiments, other devices (such as gesture analysis system(s) and/or database(s)) may be configured to perform one or more of the processes and functionalities consistent with the disclosed embodiments, including embodiments described with respect to the server.

Although particular computing devices are illustrated and networks described, it is to be appreciated and understood that other computing devices and networks can be utilized without departing from the spirit and scope of the embodiments described herein. In addition, one or more components of the network layout may be interconnected in a variety of ways, and may in some embodiments be directly connected to, co-located with, or remote from one another, as one of ordinary skill will appreciate.

The gesture analysis engine(s) may be implemented as one or more computers storing instructions that, when executed by processor(s), analyze input data from a user device and/or a wearable device in order to detect and/or monitor a predetermined gesture, and to provide information (e.g., recommendations) to assist the user in managing behavior associated with the predetermined gesture. The gesture analysis engine(s) may also be configured to store, search, retrieve, and/or analyze data and information stored in one or more databases. The data and information may include raw data collected from accelerometers and gyroscopes on one or more wearable devices, as well as each user's historical behavioral pattern and social interactions relating to the type of behavior (e.g., smoking). In some embodiments, server 106 may be a computer in which the gesture analysis engine is implemented.

However, in some embodiments, one or more gesture analysis engine(s) 108 may be implemented remotely from server 106. For example, a user device may send a user input to server 106, and the server may connect to one or more gesture analysis engine(s) 108 over network 112 to retrieve, filter, and analyze data from one or more remotely located database(s) 110. In other embodiments, the gesture analysis engine(s) may represent software that, when executed by one or more processors, perform processes for analyzing data to detect and/or monitor a predetermined gesture, and to provide information (e.g., recommendations) to assist the user in managing or overcoming certain types of behaviors.

A server may access and execute gesture analysis engine(s) to perform one or more processes consistent with the disclosed embodiments. In certain configurations, the gesture analysis engine(s) may be software stored in memory accessible by a server (e.g., in memory local to the server or remote memory accessible over a communication link, such as the network). Thus, in certain aspects, the gesture analysis engine(s) may be implemented as one or more computers, as software stored on a memory device accessible by the server, or a combination thereof. For example, one gesture analysis engine(s) may be a computer executing one or more gesture recognition techniques, and another gesture analysis engine(s) may be software that, when executed by a server, performs one or more gesture recognition techniques.

The functions of the gesture analysis engine, and its communication with the user device and wearable device, will be described in detail below with reference to FIG. 2. Although various embodiments are described herein using monitoring or cessation of smoking behavior as an example, it should be noted that the disclosure is not limited thereto, and can be used to monitor other types of behaviors and activities besides smoking.

Figure 2:
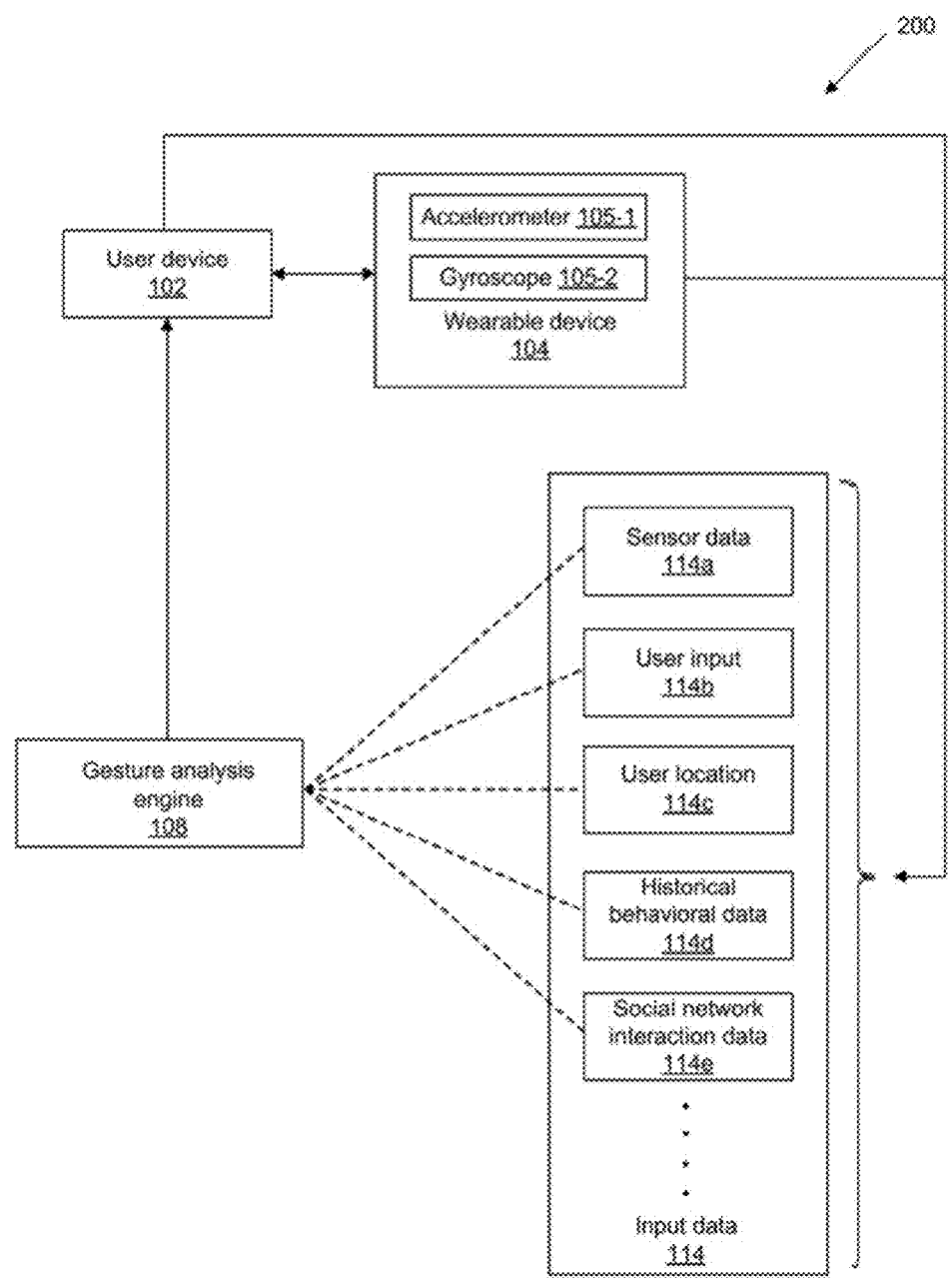
FIG. 2 illustrates exemplary components in a healthcare monitoring system, in accordance with some embodiments.

FIG. 2 illustrates exemplary components in a healthcare monitoring system in accordance with some embodiments. Referring to FIG. 2, a healthcare monitoring system 200 may comprise a user device 102, a wearable device 104, and a gesture analysis engine 108. As previously described, the gesture analysis engine may be implemented both inside and/or outside of a server. For example, the gesture analysis engine may be software and/or hardware components included with a server, or remote from the server. In some embodiments, the gesture analysis engine (or one or more functions of the gesture analysis engine) may be implemented on the user device and/or wearable device. Alternatively, the user device, wearable device, and/or server may be configured to perform different functions of the gesture analysis engine. Optionally, one or more functions of the gesture analysis engine may be duplicated across the user device, wearable device, and/or server.

In the example of FIG. 2, wearable device 104 may comprise at least one sensor 105. For example, the wearable device may comprise an accelerometer 105-1 and a gyroscope 105-2. One or more other types of sensors as described elsewhere herein may be incorporated into the wearable device.

The user device and/or the wearable device may be configured to provide input data 114 to the gesture analysis engine. The input data may comprise sensor data 114a, user input 114b, user location 114c, historical behavioral data 114d, and social network interaction data 114e.

The sensor data may comprise raw data collected by the accelerometer and the gyroscope on the wearable device. The sensor data may be stored in memory located on the wearable device, user device, and/or server. In some embodiments, the sensor data may be stored in one or more databases. The databases may be located on the server, user device, and/or wearable device. Alternatively, the databases may be located remotely from the server, user device, and/or wearable device.

The user input may be provided by a user via the user device and/or the wearable device. The user input may be in response to questions provided by the gesture analysis engine. Examples of questions may include whether the user is currently smoking, whether the user had smoked within a predetermined time period (e.g., within the last 8 hours), number of cigarettes smoked within a predetermined time period, time and place where the user had smoked, brand of cigarette, whether the user had planned to smoke that cigarette, whether the user is smoking alone or with others, how the user is feeling at a particular moment with relation to smoking, etc. The user's responses to those questions may be used to supplement the sensor data to determine the probability of a current or future smoking episode, and predict where/when the user is likely to smoke. This information obtained from the user input can be analyzed using machine learning processes.

The user location may be determined by a location sensor (e.g., GPS receiver) on the user device and/or the wearable device. The user location may be used to determine places where the user is smoking or is likely to smoke. The user location may also be used to supplement the sensor data to determine the probability of a current or future smoking episode.

The historical behavioral data may correspond to smoking-related data collected over a predetermined time period. The historical behavioral data may be stored in memory located on the wearable device, user device, and/or server. In some embodiments, the historical behavioral data may be stored in one or more databases. The databases may be located on the server, user device, and/or wearable device. Alternatively, the databases may be located remotely from the server, user device, and/or wearable device.

The social network interaction data may be obtained from an application (e.g., a mobile application) provided by the gesture analysis engine. The application may allow a user to pick a social group within the application and to compare his/her performance to other users in the social group. The social group may be defined by the users. The users in the social group may be seeking to manage or control a certain type of behavior or habit (e.g., smoking) using the application. The user's performance may include the user's successes and/or failures in managing the type of behavior or habit, compared to other users in the group.

The gesture analysis engine may be configured to obtain sensor data from at least one sensor located on the wearable device and/or the user device. For example, the gesture analysis engine may be configured to obtain sensor data from the accelerometer and/or gyroscope located on the wearable device. As previously mentioned, the wearable device may be worn by a user (e.g., on the user's wrist). The gesture analysis engine may be further configured to analyze the sensor data to determine a probability of the user performing a predefined gesture. The probability may be determined based in part on a magnitude of a motion vector in the sensor data, and without comparing the motion vector to one or more physical motion profiles.

Types of Gestures

A predefined gesture may be associated with and unique to at least one of the following activities: smoking, drinking, eating, shaving, brushing teeth, nails biting, vomiting, or chronic coughing. The gesture analysis engine may be configured to determine a probability of a user performing one or more of the above activities. The gestures associated with different activities may be differentiated from one another based at least on the magnitude of different motion vectors in the sensor data, and without comparing the motion vectors to one or more physical motion profiles.

In some cases, the gesture analysis engine may be capable of determining whether a user is drinking a hot liquid or drinking a cold liquid, based on the magnitudes of the motion vectors in the sensor data and their time durations. In other cases, the gesture analysis engine may be capable of determining a user's consumption of different types of foods, based on the magnitudes of the motion vectors in the sensor data and their time durations. For example, the gesture analysis engine can identify a hot drink or a cold drink based on number of sips, sip duration, roll, pitch etc. The gesture analysis engine can also identify the general type of food that is being consumed (e.g., whether the user is drinking soup with a spoon, eating solid food with knife and fork, eating snacks, using chopsticks, etc.). Accordingly, the gesture analysis engine may be capable of detecting various subcategories within each activity.

In some cases, the predefined gesture may be associated with a neurological disorder that causes repetitive movement and/or vibration of an extremity of the user. The gesture analysis engine may be configured to determine a probability of a user performing the predefined gesture, so as to determine an extent to which the user is suffering from the neurological disorder.

Sensor Data

As previously mentioned, an accelerometer may be disposed on the wearable device. In some embodiments, the accelerometer may be a multi-axis accelerometer such as an n-axis accelerometer, whereby n may be an integer that is equal to or greater than 2. For example, in some embodiments, the accelerometer may be a 3-axis accelerometer. The accelerometer may be able of measuring acceleration along an X-axis, a Y-axis, and a Z-axis in a local coordinate system that is defined relative to the wearable device.

Accordingly, in those embodiments, the motion vector in the sensor data may be an acceleration vector, and the magnitude of the motion vector may correspond to a magnitude of the acceleration vector. The acceleration vector may comprise a plurality of acceleration components measured along different axes of the accelerometer. For example, the plurality of acceleration components along the X-axis, Y-axis, and Z-axis may be given by Ax, Ay, and Az, respectively. Each of the acceleration components may be a vector quantity. The magnitude of the acceleration vector may be given by $A_m = SQRT(A_x^2 + A_y^2 + A_z^2)$. The magnitude of the acceleration vector may be a scalar quantity.

The gesture analysis engine may be configured to determine the probability of the user performing the predefined gesture based in part on the magnitude of the accelerator vector. For example, the gesture analysis engine may be configured to determine the probability based in part on the magnitude of the acceleration vector within different temporal periods, and without comparing the acceleration vector (and/or each acceleration component in the acceleration vector) to one or more physical motion profiles.

In some embodiments, a pitch angle and/or a roll angle of the wearable device may be calculated by the gesture analysis engine using the acceleration components along the X-axis, Y-axis, and Z-axis. In some cases, the pitch angle may be given by $\theta = \arctan[A_y/SQRT(A_x^2 + A_z^2)]$. In some embodiments, a roll angle of the wearable device may be calculated using the acceleration components along the X-axis and Z-axis. In some cases, the roll angle may be given by $\phi=\arctan[-A_x/A_z]$. The pitch angle and the roll angle may be indicative of a rotational motion of a portion of the user's body (where the wearable device is worn) about the Y-axis and the X-axis, respectively. In some embodiments, the gesture analysis engine may be configured to determine the probability of the user performing the predefined gesture based in part of the pitch angle and/or the roll angle.

As previously mentioned, a gyroscope may also be disposed on the wearable device. In those embodiments, the motion vector in the sensor data may be an angular velocity vector, and the magnitude of the motion vector may correspond to a magnitude of the angular velocity vector. The angular velocity vector may comprise a plurality of angular velocity components measured along different axes of the gyroscope.

The gesture analysis engine may be configured to determine the probability of the user performing the predefined gesture based in part on the magnitude of the angular velocity vector, and without comparing the angular velocity vector to one or more physical motion profiles. For example, the gesture analysis engine may be configured to determine the probability based in part on the magnitude of the angular velocity vector within different temporal periods.

Figure 3:
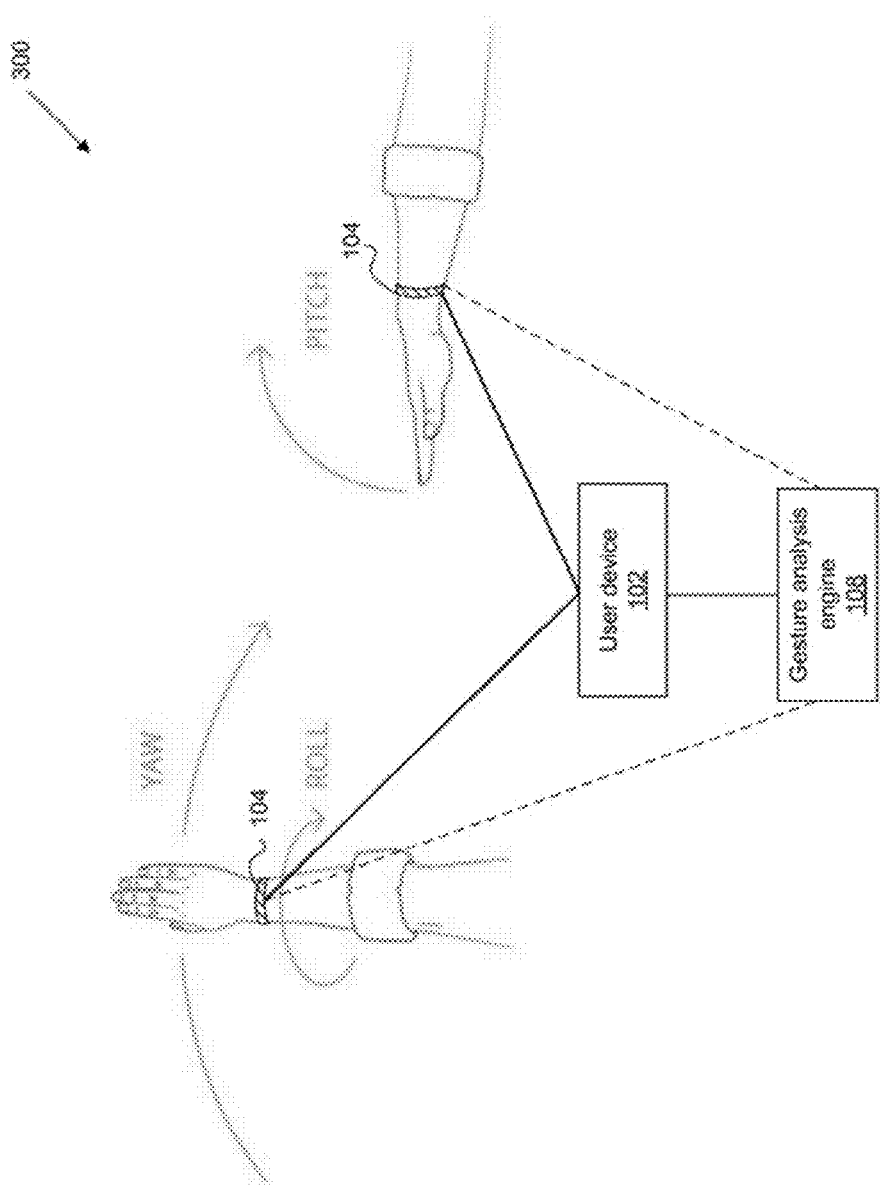
FIG. 3 illustrates the determination of a pitch angle, a roll angle, and/or a yaw angle of a wearable device based on sensor data from a gyroscope and/or an accelerometer on the wearable device, in accordance with some embodiments.

In some embodiments, as shown in FIG. 3, a pitch angle, a roll angle, and/or a yaw angle of the wearable device may be determined based on sensor data from the gyroscope and/or the accelerometer on the wearable device. The pitch angle, the roll angle, and/or the yaw angle may be indicative of a rotational motion of a part of the user's body about an X-axis, a Y-axis, and a Z-axis in a local coordinate system that is defined on the wearable device. In FIG. 3, the pitch angle may be indicative of a rotational motion of the user's wrist about the Y-axis, the roll angle may be indicative of a rotational motion of the user's wrist about the X-axis, and the yaw angle may be indicative of a rotational motion of the user's wrist about the Z-axis. The sensor data from the wearable device may be transmitted to the user device, which may subsequently transmit the sensor data to the gesture analysis engine. In some embodiments, the sensor data from the wearable device may be transmitted directly to the gesture analysis engine without going through the user device. The gesture analysis engine may be configured to determine the probability of the user performing the predefined gesture based in part on the pitch angle, the roll angle, and/or the yaw angle.

In some embodiments, the gesture analysis engine may be configured to determine the probability of the user performing the predefined gesture based in part on the magnitude of the acceleration vector and the magnitude of the angular velocity vector, and without comparing the acceleration vector and the angular velocity vector to one or more physical motion profiles. As previously mentioned, the predefined gesture may be associated with and unique to activities such as smoking, drinking, brushing teeth, and drinking. The gesture analysis engine may be configured to determine a probability of a user performing one or more of the above activities. The gestures associated with different activities may be differentiated from one another based at least on the magnitude of different motion vectors in the sensor data, and without comparing the motion vectors to one or more physical motion profiles.

Figure 4:
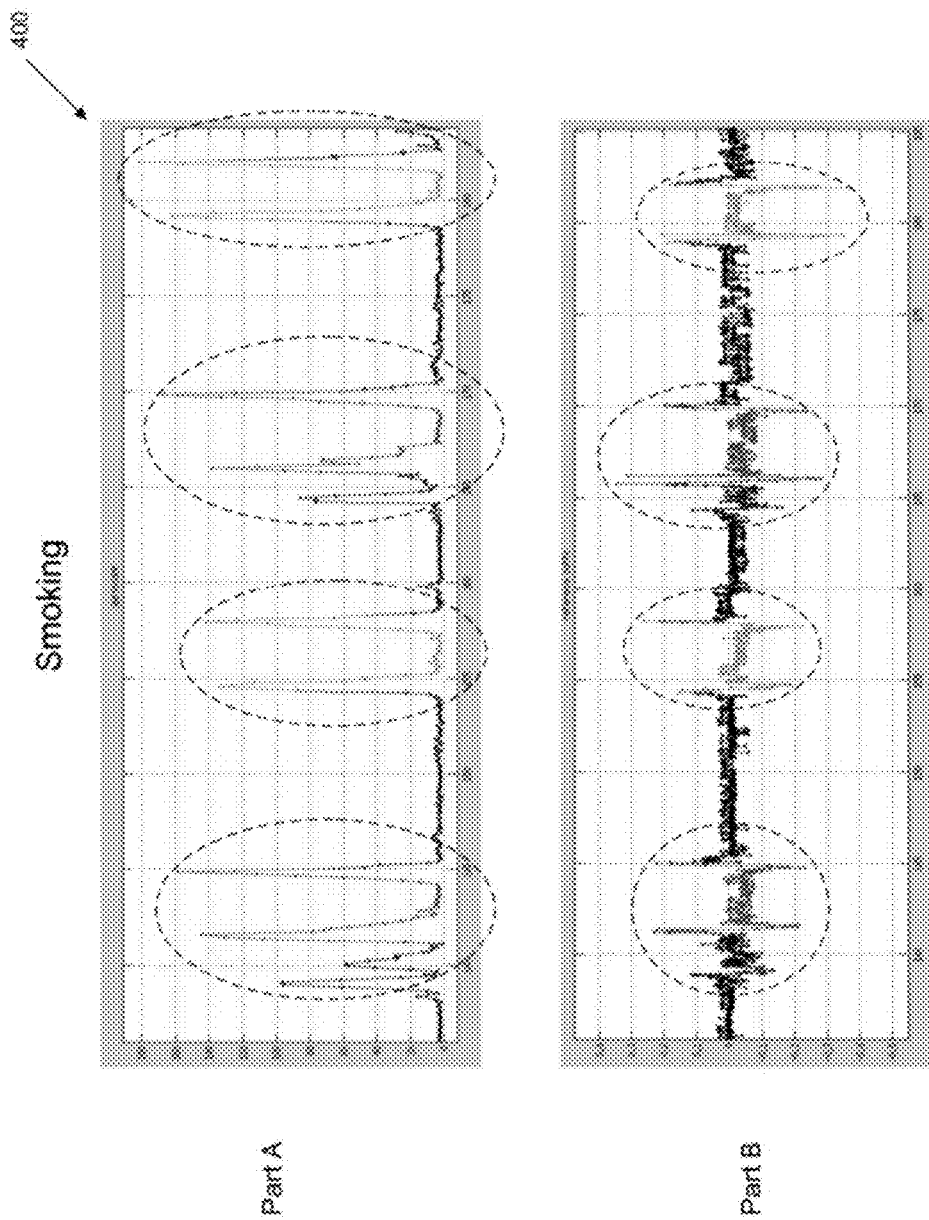
FIG. 4 illustrates the correlation in magnitude of an angular velocity vector to a reference as a user is smoking, in accordance with some embodiments.

FIGS. 4, 5, 6, and 7 illustrate the data collected by an accelerometer and a gyroscope on a wearable device as a user is performing different activities (gestures), in accordance with some embodiments. For example, parts A and B of FIG. 4 respectively illustrate the magnitudes of the angular velocity vector and the acceleration vector as a user is smoking. As shown in FIG. 4, the magnitudes of the angular velocity vector in part A and the acceleration vector in part B show a temporal correlation, as indicated by the circled regions. By comparing the magnitudes of the angular velocity vector in part A to the acceleration vector in part B over different temporal periods, the gesture analysis engine can determine a probability that the user's gesture corresponds to smoking. For example, in FIG. 4, the data may indicate that the user has taken four cigarette puffs (as indicated by the four circled regions in part A).

The above analysis may be extended to other types of behaviors or activities. For example, parts A and B of FIG. 5 respectively illustrate the magnitudes of the acceleration vector and the angular velocity vector as a user is eating. The circled regions in parts A and B of FIG. 5 illustrate a correlation between the magnitudes of the acceleration vector and the angular velocity vector as the user is eating.

Figure 6:
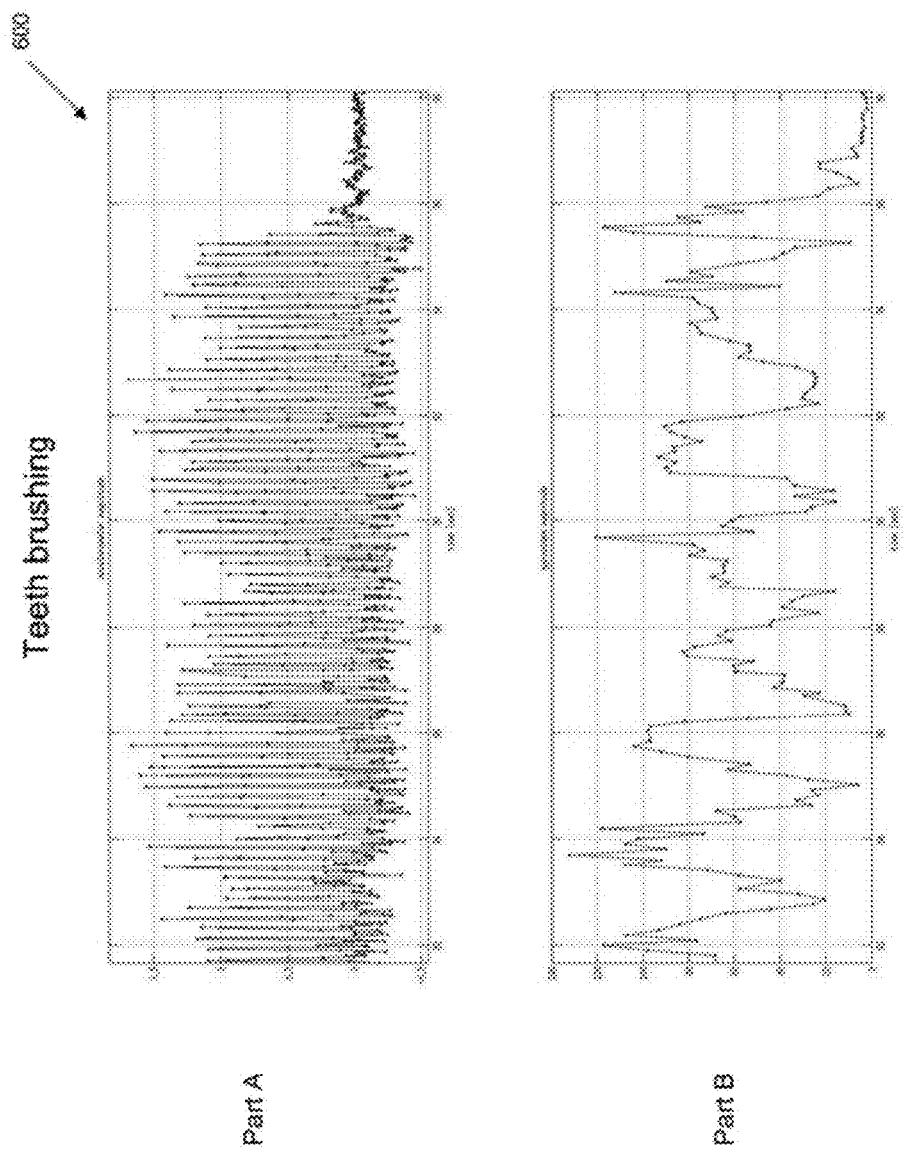
FIG. 6 illustrates the correlation in magnitudes of the acceleration vector and the angular velocity vector as a user is brushing teeth, in accordance with some embodiments.

Parts A and B of FIG. 6 respectively illustrate the magnitudes of the acceleration vector and the angular velocity vector as a user is brushing teeth. In FIG. 6, although the magnitude of the acceleration vector changes at high frequency (shown in part A), it may be observed that the magnitude of the angular velocity vector changes at a lower frequency. A correlation can still be made because this magnitude pattern of the acceleration vector and angular velocity vector may be unique to teeth-brushing.

Figure 7:
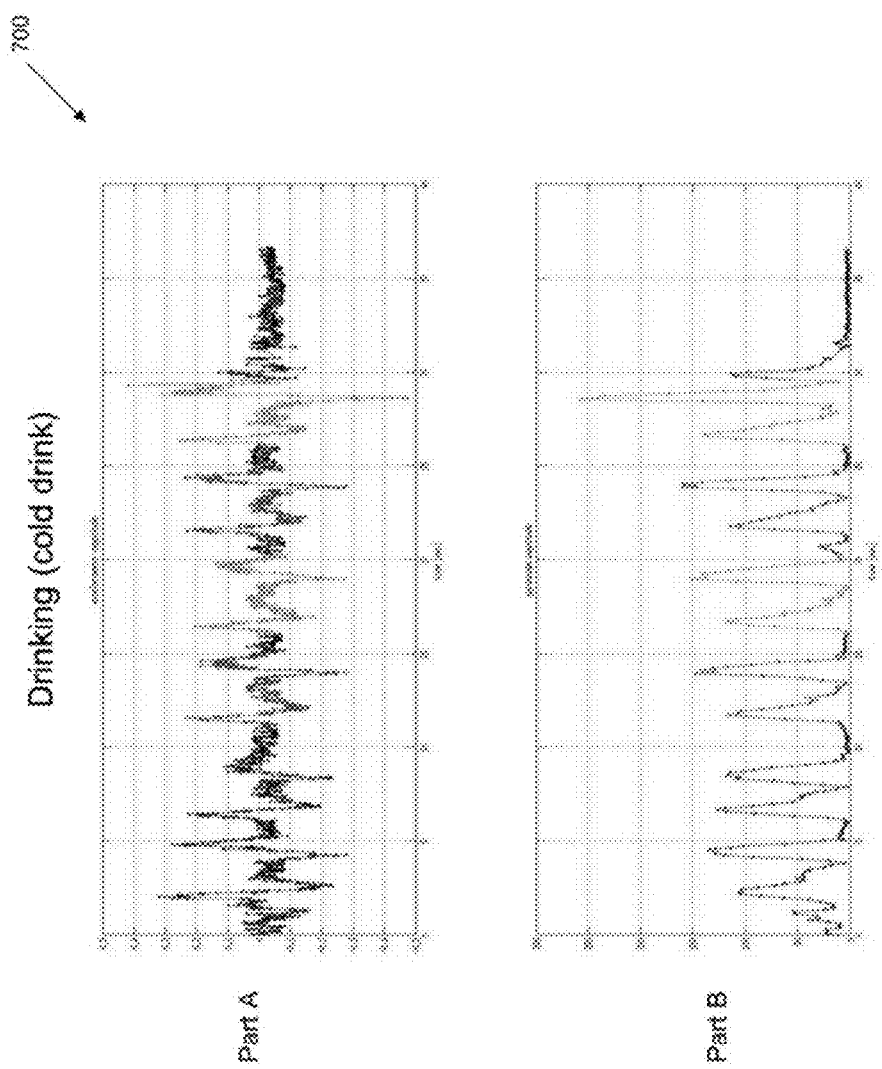
FIG. 7 illustrates the correlation in magnitudes of the acceleration vector and the angular velocity vector as a user is drinking a cold drink, in accordance with some embodiments.

Parts A and B of FIG. 7 respectively illustrate the magnitudes of the acceleration vector and the angular velocity vector as a user is drinking a cold drink. As shown in FIG. 7, there is also a correlation between the magnitudes of the acceleration vector and the angular velocity vector.

Figure 5:
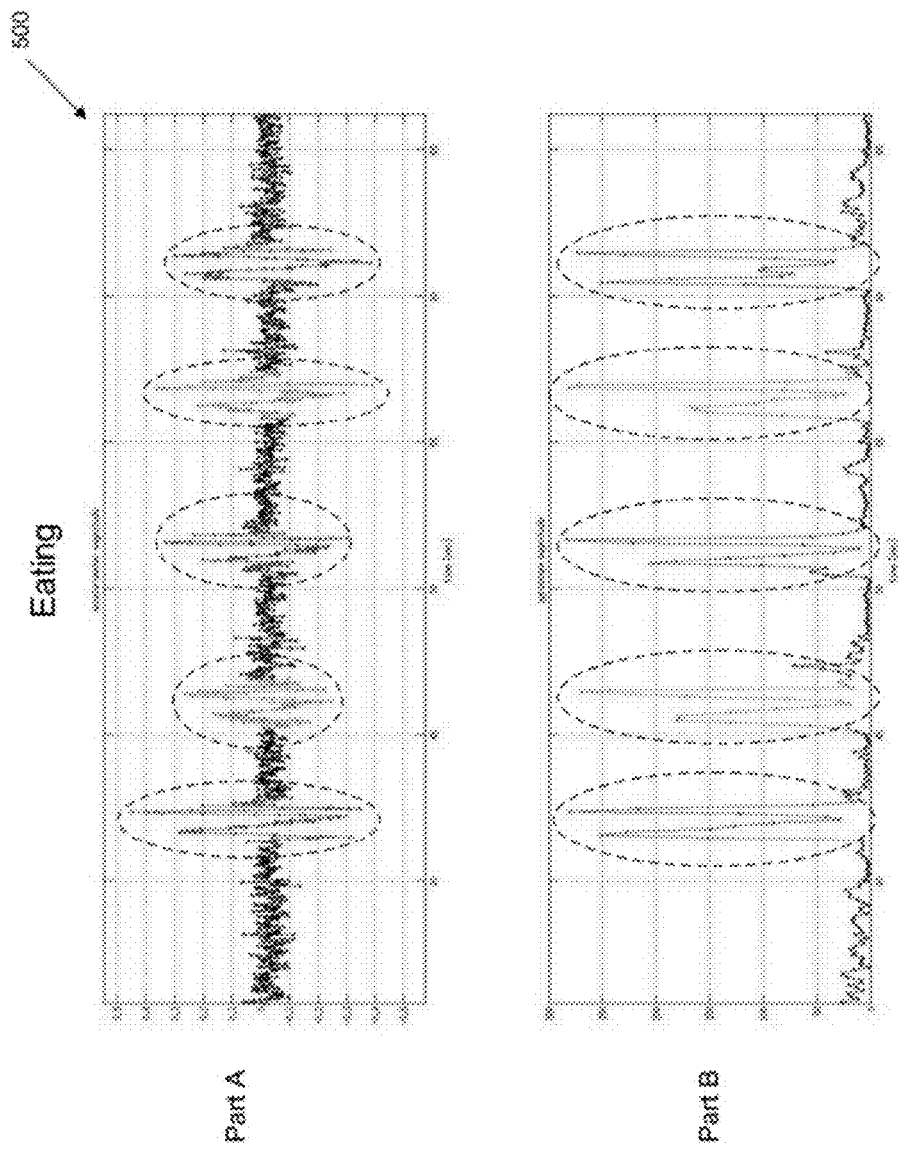
FIG. 5 illustrates the correlation in magnitudes of the acceleration vector and the angular velocity vector as a user is eating, in accordance with some embodiments.

Comparing FIGS. 5, 6, and 7, it may be observed that the magnitudes of the acceleration vector and the angular velocity vector are different (and vary at different frequencies) between the different activities, and therefore can be used to distinguish among the different activities. In particular, by comparing the magnitudes of the vectors alone across different temporal periods, and without comparing the vectors to actual physical motion profiles (or patterns), the processing power and/or time needed to detect a gesture associated with the behavior/activity can be reduced, according to various embodiments described in this disclosure.

Figure 8:
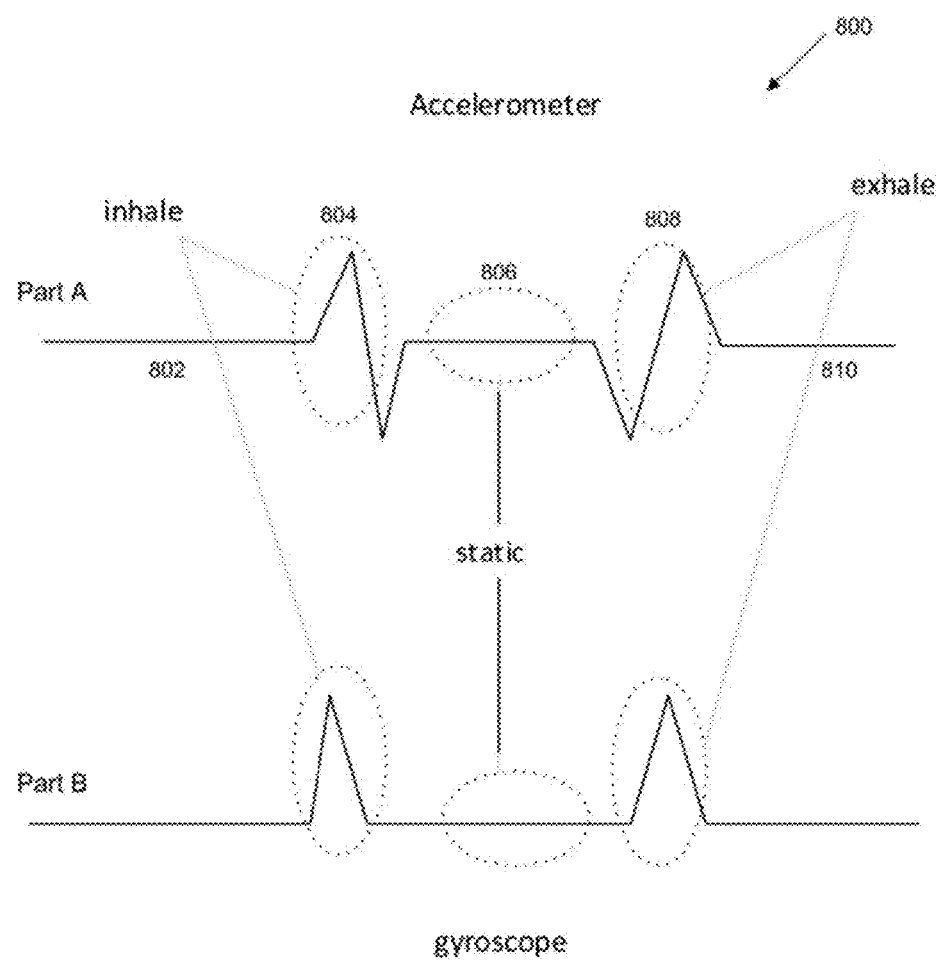
FIG. 8 illustrates the correlation in magnitudes of the acceleration vector and the angular velocity vector during a smoking episode (for a single puff), in accordance with some embodiments.

In some embodiments, the gesture analysis engine may be configured to determine a correlation between the magnitudes of the acceleration vector and the angular velocity vector within same/different temporal periods, so as to determine the probability of the user performing the predefined gesture. FIG. 8 illustrates the data collected by an accelerometer and a gyroscope on a wearable device as a user is smoking, in accordance with some embodiments. Parts A and B of FIG. 8 respectively illustrate the magnitudes of the acceleration vector and the angular velocity vector when the user is smoking (for a single puff). During a single puff in a smoking episode, the user may first bring the cigarette to the mouth (hand-to-mouth gesture), inhale (take a puff), remove the cigarette from the mouth (mouth-to-hand gesture), and exhale. In region 802 of FIG. 8, the user's hand may be in a rest position. In region 804, the user may be bringing the cigarette to the mouth. In region 806, the user may be taking a puff (inhaling). In region 808, the user may be removing the cigarette from the mouth and exhaling. In region 810, the user's hand may be again in a rest position. As shown in FIG. 8, the magnitudes of the acceleration vector and the angular velocity vector may show a correlation for each submotion of the smoking gesture.

Statistical Analysis of Sensor Data to Determine Probability of User Performing a Predefined Gesture The gesture analysis engine may be configured to analyze the sensor data against one or more physical motion profile patterns. A physical motion profile pattern as used herein may refer to any pattern that has substantially a same profile as a corresponding physical gesture of a user. A shape of the physical motion profile pattern may be substantially similar to a shape of the corresponding physical gesture of the user. For example, if a user physically makes an L-shaped gesture, a corresponding physical motion profile pattern may have substantially an L-shape.

In some embodiments, the gesture analysis engine may be configured to calculate a multi-dimensional distribution function that is a probability function of a plurality of features in the sensor data. The features may be extracted from the sensor data. The plurality of features may comprise n number of features denoted by $p_1$ through $p_n$, where n may be any integer greater than 1. The multi-dimensional distribution function may be denoted by $f(p_1, p_2, \ldots, p_n)$.

The plurality of features may be associated with various characteristics of the predefined gesture. For example, in some embodiments, the plurality of features may comprise two or more of the following features: (1) a time duration of a submotion during the gesture; (2) the magnitude of the acceleration vector; (3) the magnitude of the angular velocity vector; (4) the roll angle; (5) the pitch angle; and/or (6) the yaw angle. The submotion may be, for example, a hand-to-mouth gesture and/or a mouth-to-hand gesture. Accordingly, the multi-dimensional distribution function may be associated with one or more characteristics of the predefined gesture, depending on the type of features that are selected and analyzed by the gesture analysis engine. The multi-dimensional distribution function may be configured to return a single probability value between 0 and 1, with the probability value representing a probability across a range of possible values for each feature. Each feature may be represented by a discrete value. Additionally, each feature may be measurable along a continuum. The plurality of features may be encoded within the sensor data, and extracted from the sensor data using the gesture analysis engine 108.

In some embodiments, two or more features may be correlated. The gesture analysis engine may be configured to calculate the multi-dimensional distribution function by using Singular Value Decomposition (SVD) to de-correlate the features such that they are approximately orthogonal to each other. The use of SVD can reduce a processing time required to compute a probability value for the multi-dimensional distribution function, and can reduce the amount of data required by the gesture analysis engine to determine a high probability (statistically significant) that the user is performing the predefined gesture.

In some embodiments, the gesture analysis engine may be configured to calculate the multi-dimensional distribution function by multiplying the de-correlated (rotated) 1D probably density distribution of each feature, such that the multi-dimensional distribution function $f(p_1, p_2, \ldots, p_n) = f(p_1)*f(p_2)* \ldots *f(p_n)$. The function $f(p_1)$ may be a 1D probability density distribution of a first feature, the function $f(p_2)$ may be a 1D probability density distribution of a second feature, the function $f(p_3)$ may be a 1D probability density distribution of a third feature, and the function $f(p_n)$ may be a 1D probability density distribution of a n-th feature. The 1D probability density distribution of each feature may be obtained from a sample size of each feature.

In some embodiments, the sample size may be constant across all of the features. In other embodiments, the sample size may be variable between different features.

In some embodiments, the gesture analysis engine may be configured to determine whether one or more of the plurality of features are statistically insignificant. For example, one or more statistically insignificant features may have a low correlation with the predefined gesture. In some embodiments, the gesture analysis engine may be further configured to remove the one or more statistically insignificant features from the multi-dimensional distribution function. By removing the one or more statistically insignificant features from the multi-dimensional distribution function, a computing time and/or power required to calculate a probability value for the multi-dimensional distribution function can be reduced.

Smoking Statistics Example

In some embodiments, the gesture analysis engine may be configured to analyze the sensor data to determine a probability that a user smoking. The probability may be determined based in part on a magnitude of an acceleration vector and/or an angular velocity vector in the sensor data, and without comparing the acceleration vector and/or the angular velocity vector to one or more physical motion profiles. In those embodiments, the gesture analysis engine may be configured to analyze one or more features in the sensor data to determine a probability of the user taking a cigarette puff The features may comprise at least one of the following: (1) a time duration that a potential cigarette is detected in a mouth of the user; (2) a roll angle of the user's arm; (3) a pitch angle of the smoker's arm; (4) a time duration of a potential smoking puff; (5) a time duration between consecutive potential puffs; (6) number of potential puffs that the user takes to finish smoking a cigarette; (7) the magnitude of the acceleration vector; (8) a speed of the user's arm; (9) an inhale region corresponding to an arm-to-mouth gesture; and (10) an exhale region corresponding to an arm-down-from-mouth gesture.

The gesture analysis engine may extract the features from the sensor data and insert them into a mathematical function to obtain the confidence (0-100%) level for which these features match a smoking gesture. If the confidence level is high, the gesture analysis engine may determine that the user has smoked a cigarette. The mathematical function represents the user statistics. Different users have different statistics and functions. A mathematical function may be represented by its polynomial coefficients (a's). Accordingly, the function may be defined by a set of numbers (a's). For example, in the equation show below, P is the function, x is the feature inserted into the function, and a's are the coefficients that represent the function.

$$P(x) = \sum_{i=0}^{n} a_i x^i = a_0 + a_1 x + a_2 x^2 + \cdots + a_{n-1} x^{n-1} + a_n x^n, n \geq 0$$

In some embodiments, the gesture analysis engine may be configured to calculate a multi-dimensional distribution function associated with one or more smoking characteristics. The one or more smoking characteristics may be associated with a user taking a cigarette puff. The gesture analysis engine may be configured to generate a multi-dimensional distribution function for each puff The gesture analysis engine may be configured to determine the probability of the user smoking based on: (1) a number of potential puffs; (2) the multi-dimensional distribution function for each potential puff; and (3) a time duration in which the number of potential puffs occur. The gesture analysis engine may be configured to determine whether a sum of the multi-dimensional distribution functions for a number of potential puffs is equal to or greater than a predetermined probability threshold. For example, the gesture analysis engine may determine that the user is smoking when the sum is equal to or greater than the predetermined probability threshold, and that the user is not smoking when the sum is less than the predetermined probability threshold. In some embodiments, the gesture analysis engine may determine that the user is smoking when a predetermined number of puffs have been detected within a predetermined time period. For in some cases, the predetermined number of puffs may be at least three puffs, and the predetermined time period may be about five to six minutes. The gesture analysis engine may be configured to analyze the roll and pitch angles associated with the potential puffs, and discard those puffs whose roll and pitch angles fall outside of a predetermined roll/pitch threshold. The gesture analysis engine may also be configured to analyze a time duration between the potential puffs, and discarding the puffs where the time duration falls outside of a predetermined time period.

Figure 9:
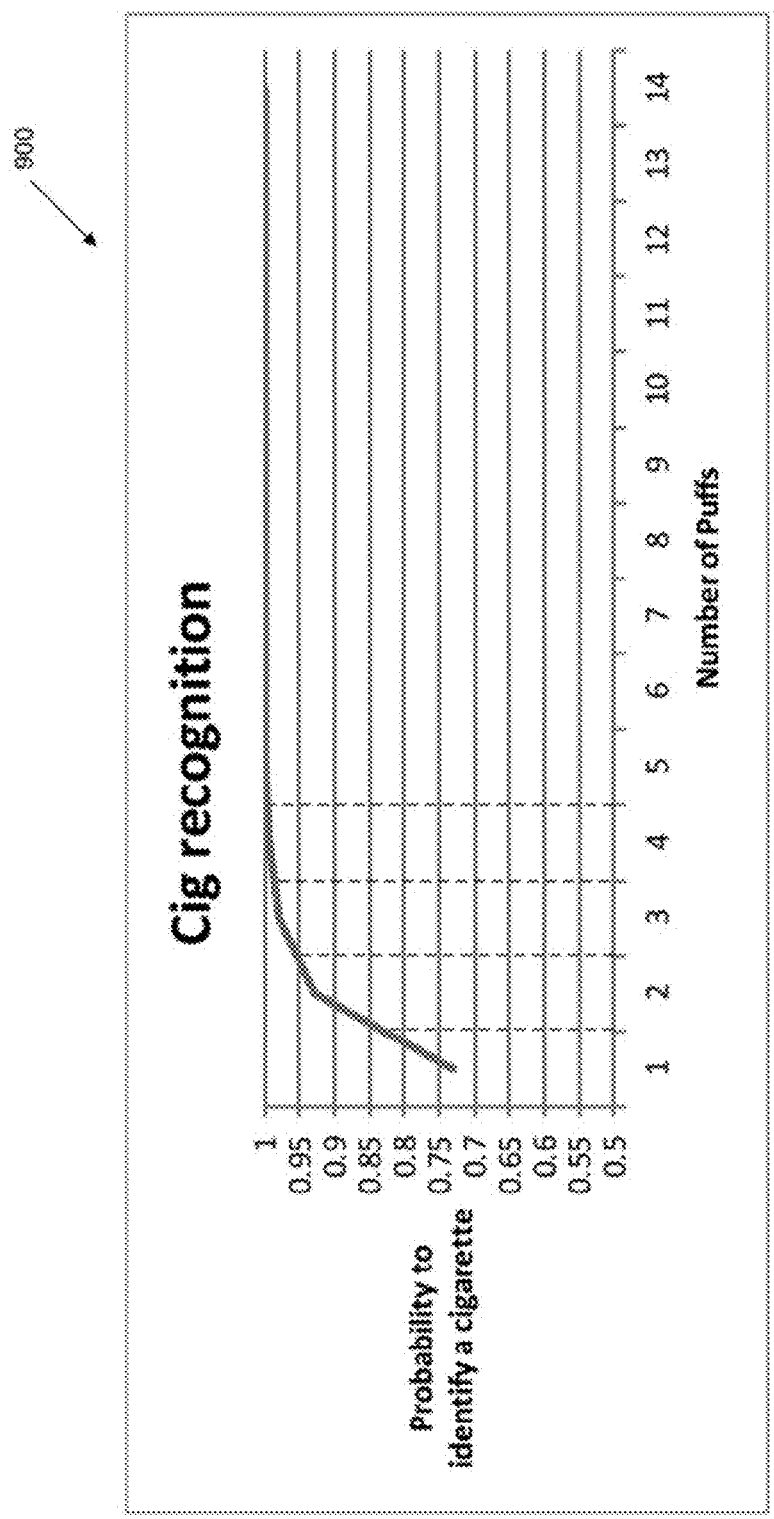
FIG. 9 is graph of the probability that a user is smoking a cigarette as a function of number of smoking puffs, in accordance with some embodiments.

FIG. 9 is graph of the probability that a user is smoking a cigarette as a function of number of smoking puffs, in accordance with some embodiments. A gesture analysis engine (e.g., gesture analysis engine) may be configured to analyze the sensor data to determine a probability that a user smoking. In some cases, as shown in FIG. 9, the gesture analysis engine may determine a probability of about 83% that a user is smoking, based on a first puff. The first puff may be an actual cigarette puff. When the user takes a second puff, the gesture analysis engine may determine a probability of about 95% that the user is actually smoking. By the time the user takes a third puff, the gesture analysis engine may determine a probability of about 99% that the user is actually smoking. Accordingly, the gesture analysis engine may be capable of determining whether the user is smoking based on a number of potential detected puffs. In some cases, the gesture analysis engine may be capable of determining a high probability (e.g., 99%) of the user based on the first puff Adaptive Gesture Recognition As previously described, the input data may comprise user input provided by a user. The gesture analysis engine may be configured adjust the probability of the user smoking based on one or more user inputs. The user inputs may comprise: (1) an input signal indicating that the user did not smoke; (2) an input signal indicating that the user had smoked; and (3) an input signal indicating that the user had smoked but the smoking gesture was not recognized or detected.

In some embodiments, the gesture analysis engine may implement an algorithm with a broad statistics that fit the average person (everyone) for a specific type of behavior or gesture. The algorithm can be configured to adapt the statistics to a specific person over time. Each person may subsequently have a unique configuration file with his/her personal statistics, as described below.

For example, the gesture analysis engine may be configured to generate a user configuration file (UCF) for the user based on the analyzed sensor data and the one or more user inputs. Initially, the gesture analysis engine may generate a general UCF. The general UCF may be generic and non-specific to any user. The general UCF may comprise a list of user parameters associated with smoking. Additionally, the general UCF may comprise a list of user parameters associated with different activities besides smoking. Examples of those activities may comprise at least one of the following: standing, walking, sitting, driving, drinking, eating, and leaning while either standing or sitting. The leaning may be associated with the user's elbow. For example, the user may be sitting and leaning an elbow on an object. In some embodiments, the gesture analysis engine may be configured to generate a left hand UCF and/or right hand UCF for the user in addition to the general UCF. In some embodiments, the left hand UCF and/or right hand UCF may be incorporated in the general UCF.

The UCF may be configured to adapt and change over time depending on the user's behavior. Accordingly, after the gesture analysis engine has collected and analyzed historical behavioral data of the user for some time, the gesture analysis engine may generate a personal UCF that is unique to the user, based on changes to the general UCF and/or the left/right hand UCFs.

In some embodiments, the gesture analysis engine may be configured to dynamically change the general UCF, left/right UCF, and/or personal UCF when the system detects that the user has not performed a predefined gesture for a predetermined time period. For example, one or more of the above UCFs may be dynamically changed when the system detects that the user has not smoked for a predetermined time period. In some embodiments, the system may send a question or prompt to the user (on user device and/or wearable device) requesting the user to verify that he/she has not smoked for the predetermined time period.

In some embodiments, the gesture analysis engine may be configured to determine whether the user is smoking with a right hand or a left hand based on roll angle and pitch angle obtained from the sensor data. In those embodiments, the gesture analysis engine may be configured to update the left/right hand UCFs with the left/right hand information of the user.

Delivery of Personalized Information

In some embodiments, the gesture analysis engine may be configured to include additional features (besides those from the sensor data) into the multi-dimensional distribution function. For example, those additional features may be associated with the user input, the user location, historical behavioral data of the user, and/or social network interaction of the user. Those additional features may be extracted from data that is not sensor-based.

The gesture analysis engine may be configured to analyze the input data using one or more statistical functions, and to provide the analyzed data to the gesture analysis engine. The gesture analysis engine may include natural language processing (NLP) clustering and/or machine learning capabilities. NLP clustering may be based on machine learning, for example statistical machine learning. The statistical machine learning may be based on statistical inference. The gesture analysis engine may be configured to learn metrics or characteristics associated with a predefined gesture, and to determine a user's progress in managing certain types of behavior. This machine learning may be accomplished the gesture analysis engine by analyzing large corpora of real-world input stored in one or more databases. The gesture analysis engine may include statistical models capable of making soft, probabilistic decisions that are based on attaching real-valued weights to behavioral gesture, depending on its context (e.g., where and when the gesture was performed, and under what circumstances). The statistical models may be robust to unfamiliar input (e.g. new arm motions of a user) and to erroneous input (e.g. false detection of a gesture).

The gesture analysis engine may be configured to deliver personalized information (e.g., recommendations) to a user, by transmitting the information to the user device and/or the wearable device. The information may be subsequently displayed to the user on the user device and/or the wearable device. A user may rely on the information to monitor certain types of behavior. In some embodiments, the gesture analysis engine may be configured to proactively provide guidance to assist a user in managing certain types of behavior, based on the input data provided to the gesture analysis engine and the gesture analysis engine.

In some embodiments, the gesture analysis engine may be configured to analyze the user's social network interaction using an application (e.g., a mobile application) provided by the gesture analysis engine. The application may allow a user to pick a social group within the application and to compare his/her performance to other users in the social group. The social group may be defined by the users. The users in the social group may be seeking to manage or control a certain type of behavior or habit (e.g., smoking) using the application. The user's performance may include the user's successes and/or failures in managing the type of behavior or habit, compared to other users in the group. In some embodiments, by extrapolating data in the social group and over different timelines, the gesture analysis engine can more accurately monitor the user's progress and provide personalized recommendations to the user. In some embodiments, the gesture analysis engine may be configured to determine the probability of the user performing the pre-defined gesture at different times of the day and/or at different geographical locations. For example, the gesture analysis engine may be configured to determine the probability of the user smoking at different times of the day and/or at different geographical locations. In some embodiments, the gesture analysis engine may be configured to promote and advertise different products or services based on the accumulative smoking patterns of one or more users.

In some embodiments, the gesture analysis engine can dynamically provide personalized recommendations to the user in real-time. The personalized recommendations may also be provided at a predetermined frequency, e.g., every hour, 12 hours, 24 hours, 2 days, 4 days, etc. In some instances, the gesture analysis engine can provide a personalized recommendation based on the user's behavior, or when there are changes in the user's behavior (e.g., when the user is smoking a greater number or a fewer number of cigarettes compared to before).

In some embodiments, in addition to providing a user with the information that the user seeks and will most likely consume, the gesture analysis engine can further provide personalized recommendations to influence the user's needs and behavior.

During a smoking cessation program, the user's needs and challenges may vary each day. For example, the user may suffer from anxiety, depression, low spirits, lack of energy, urge to smoke, etc. Furthermore, the user may be influenced by other events such as stress and peer pressure. The gesture analysis engine can be configured to take into account the dynamic nature of the user's experiences during the smoking cessation program. For example, the gesture analysis engine can parametrize the user's behavior and body response characteristics at different timeframes. In some embodiments, the gesture analysis engine can be configured to determine the user's potential needs, and provide personalized recommendations based on those potential needs. Accordingly, in some embodiments, the gesture analysis engine may be capable of sentiment analysis, so as to more accurately construe and predict the user's needs and behavior.

In some embodiments, the analyzed data may be provided by the gesture analysis engine to a healthcare organization, an insurance company, and/or government agency. One or more of the above entities may use the data to tailor preventive behavioral programs that promote the health and well-being of the users.

Methods for Detection of Smoking Behavior

Figure 10:
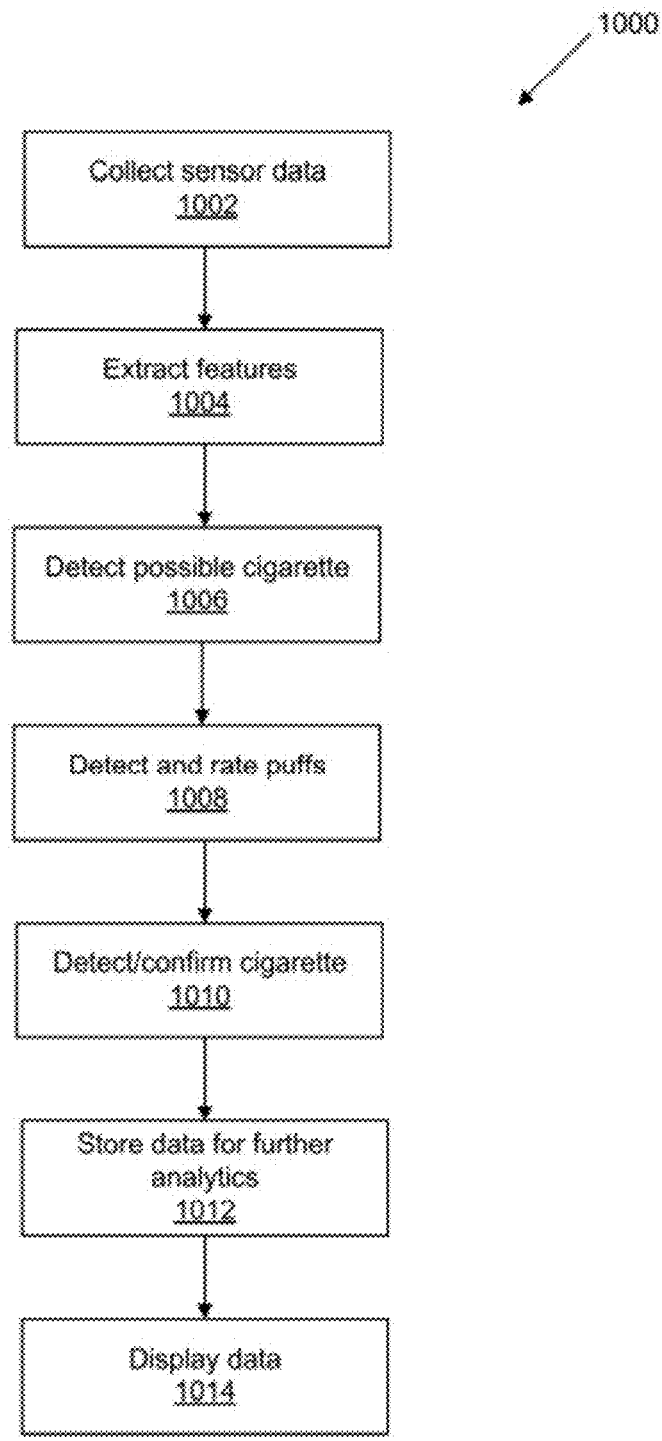
FIG. 10 is a flowchart of a method of detecting a probability of a user smoking a cigarette, in accordance with some embodiments.

FIG. 10 is a flowchart of a method 1000 of detecting a probability of a user smoking a cigarette, in accordance with some embodiments. First, sensor data may be collected by one or more sensors on the wearable device, in real-time, intermittently, at fixed or different frequencies (step 1002). The sensor data may be transmitted to the gesture analysis engine, either directly from the wearable device or via a user device. In some embodiments, the gesture analysis engine may be located on a server remote from the user device and/or the wearable device. Alternatively, the gesture analysis engine may be located on the user device and/or the wearable device. Optionally, various aspects or functions of the gesture analysis engine may be implemented using the server, user device, and/or wearable device. The gesture analysis engine may be configured to determine a probability of a user smoking based on the sensor data. The smoking behavior may consist of the user taking one or more cigarette puffs.

Some or all of the sensors on the wearable sensor may be activated at any time. In some embodiments, a subset of the sensors may be activated to reduce power consumption of the wearable device. When the gesture analysis engine and/or user device detects that the user may be taking a first potential cigarette puff (e.g., with probability <1), the gesture analysis engine and/or user device may be configured to transmit signals to the wearable sensor to turn on the other sensors. Some or all of the sensor data may be aggregated and sent in blocks from the wearable device to the gesture analysis engine in real-time (either directly or via the user device).

The gesture analysis engine may be configured to extract a set of pre-defined features from some or all of the sensor data (step 1004). The gesture analysis engine may be configured to use the set of pre-defined features to detect a probability of the user smoking, by rating a potential cigarette puff and/or number of puffs (steps 1006 and 1008). This may be achieved by analyzing the magnitudes of the acceleration vector and/or angular velocity vector of the hand-to-mouth and mouth-to-hand gestures against certain smoking models.

Based on the rated puffs, the gesture analysis engine can detect whether the user is smoking or has smoked a cigarette (step 1010). The gesture analysis engine may transmit and store smoking-related information into a database for further and/or future analysis (step 1012). The smoking-related information may comprise a duration of a cigarette puff, cigarette type, personal information of the user, location of the user, time of smoking, etc. The smoking-related information may be accumulated over time and used to generate smoking-behavioral trends of the user. The smoking-related information may be displayed on a graphical display on the user device (step 1014). The gesture analysis engine can use the smoking-behavioral trends to improve a confidence level of the statistical analysis, and to predict when/where a user is likely to smoke. For example, the gesture analysis engine may analyze the smoking-behavioral trends to detect hidden correlations between different parameters in the information. The hidden correlations may be used to predict user behavior and/or habits.

Figure 11:
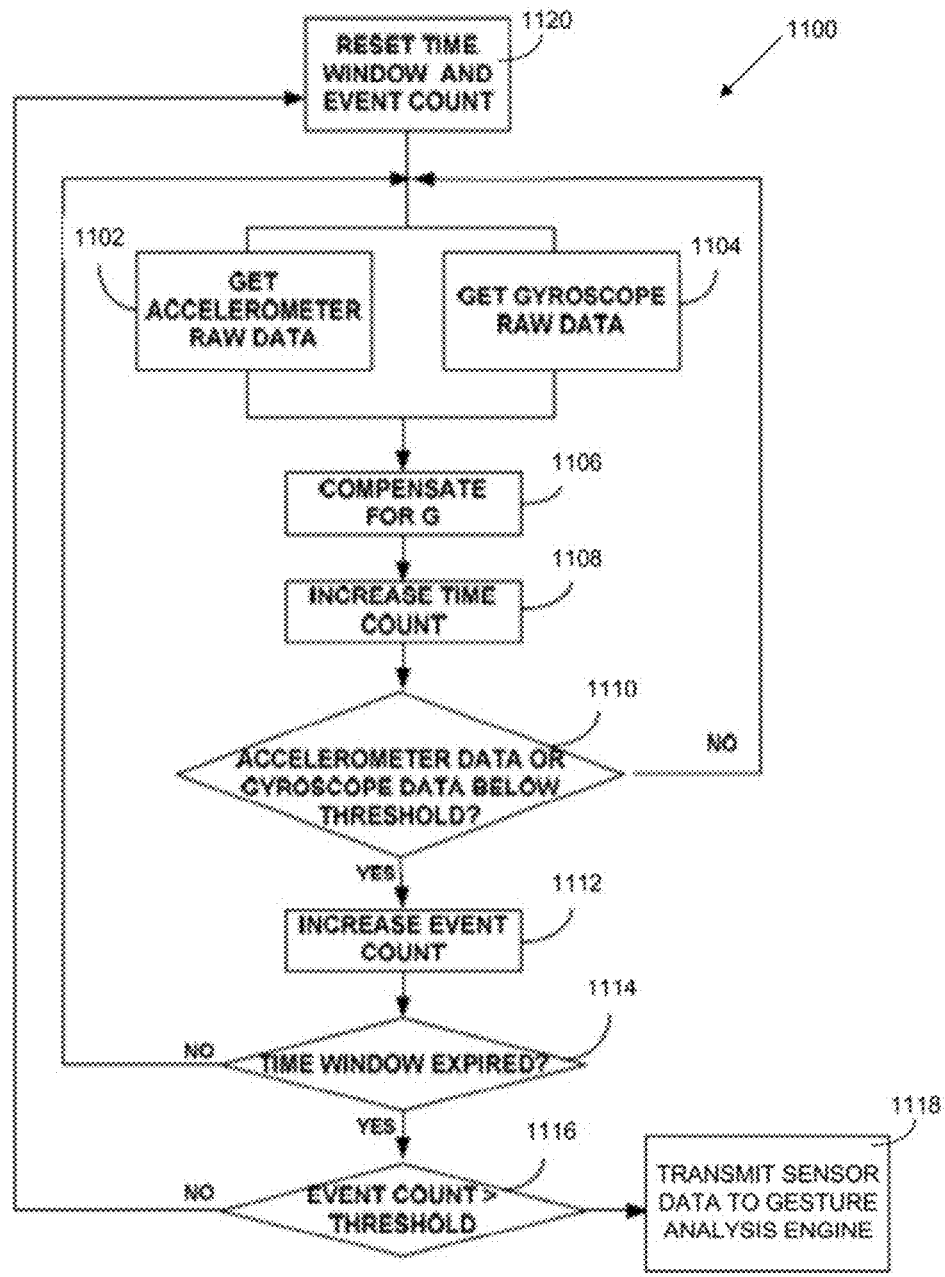
FIG. 11 is a flowchart of a method of detecting a probability of a user smoking a cigarette, in accordance with some other embodiments.

FIG. 11 is a flowchart of a method 1100 of detecting a probability of a user smoking a cigarette, in accordance with some other embodiments. First, data may be collected by an accelerometer and a gyroscope on a wearable device (steps 1102 and 1104). In some cases, the data may be adjusted to compensate for the effects of gravitational force (step 1106). In some cases, if the data is insufficient to detect a gesture, a time count (e.g., a time duration or frequency) of the sensor data collection may be increased (step 1108). The sensor data may be transmitted to a user device. The user device may be configured to monitor sensor data (e.g., accelerometer and/or gyroscope data) collected by the wearable device. The user device may be configured to look for regions in the signal where one or both signals in the accelerometer or gyroscope data are below predefined thresholds (step 1110). These regions may correspond to 'suspected puff areas'. If the one or more signals in the accelerometer or gyroscope data are below the predefined thresholds, the user device may instruct the wearable device to increase an event count (step 1112) to increase a sampling frequency (step 1112). If the one or more signals in the accelerometer or gyroscope data are above the predefined thresholds, the collection of sensor data continues at its previous sampling frequency. Next, the user device determines if a time window has expired (step 1114). If the time window has not expired, the wearable device may continue to collect sensor data. If the time window has expired, the user device may determine whether an event count is greater than a threshold count (step 1116). If the event count is less than the threshold count, the time window and event count may be reset (step 1120) so that a new set of sensor data may be collected. If the event count is greater than the threshold count, some or all of the sensor data may be transmitted to the gesture analysis engine to detect a probability of the user smoking (step 1118). For example, when a sufficient regions have been detected in a pre-defined time window (e.g., 10 minutes), the user device may transmit some or all of the sensor data (including the sensor data it has already processed) to the gesture analysis engine.

The gesture analysis engine may be configured to evaluate each puff candidate by comparing it to pre-defined statistics and rate each puff. For example, the gesture analysis engine may extract information from the puff signal (e.g., length of time a signal is low, etc.) and compare each value with a pre-defined empirical statistical model. The model may be general (the same for all smokers), or specific for each smoker. The probabilities are then aggregated into a puff rating. In some embodiments, one or more features may be extracted from the candidate puff signal and processed using machine learning algorithms to produce a puff rating. The machine learning may comprise supervised-learning, semi-supervised learning or unsupervised learning techniques.

After all the candidate puffs in a time window have been rated, the gesture analysis engine can then determine whether a cigarette was smoked. For example, the gesture analysis engine may count the puffs above a certain rating (e.g. 50%) and compare the number of puffs to a threshold (e.g. 4 puffs). If the counted number of puffs is greater than the threshold, the gesture analysis engine may determine that the user is smoking a cigarette. Conversely, if the counted number of puffs is less than the threshold, the gesture analysis engine may determine that the user is not smoking a cigarette, and may be performing some other gesture.

In some embodiments, the gesture analysis engine may be configured to process a whole cigarette signal instead of individually analyzing single puffs (e.g., a 10-minute signal instead of an 8-second signal). A whole cigarette signal may be illustrated in, for example FIG. 4. A single puff signal may be illustrated in, for example FIG. 8. The gesture analysis engine can analyze a pre-defined time window of accelerometer and/or gyroscope signals (e.g., the time it may take to smoke a cigarette may be about 10 min) and detect a user possibly smoking a cigarette based on the signals. The gesture analysis engine may be configured to determine a total time that the signal variance is below a pre-defined threshold. Alternatively, the gesture analysis engine may be configured to determine a relationship between the time that the signal variance is below the threshold and the time that it is above the threshold.

If the gesture analysis engine determines that the time is greater than a pre-defined value, the system may then determine that the user may be possibly smoking. Once a possible cigarette is detected, the entire signal can be transmitted to the gesture analysis engine. The gesture analysis engine may analyze all of the signals (instead of processing each puff separately) and rate the possible cigarette. This can be done by transforming the signals into frequency domain and extracting features (e.g., energy in specific frequencies, etc.). The gesture analysis engine can also process the signals, the signal power, and/or the signal derivative (rate of change) and extract features therefrom. The features can then be used to rate the possible cigarette. Once the cigarette is rated, the gesture analysis engine can determine whether the rating is greater than a pre-defined threshold (e.g. 50%). If the rating is above the threshold, then a cigarette is determined to have been detected. Once a cigarette is detected, the gesture analysis engine may try to estimate other puffs based on the first puff sample. In some embodiments, the gesture analysis engine may be configured to extract features from puff candidates as well as from a whole cigarette, to determine whether the user has smoked a cigarette.

In some embodiments, the gesture analysis engine may be configured to alert and inform the user of changes in behavior, patterns, goals matching and other consumption related alerts. For example, the gesture analysis engine may provide an alert when the user behavior diverges from the user's typical behavior or historical behavior. For example, the gesture analysis engine may detect that a user normally smokes 2 cigarettes in the morning and 2 cigarettes in the evening. When the system detects that the user started smoking 2 additional cigarettes at noon, the system may send an alert to the user so that the user may refrain from smoking the additional cigarettes.

Figure 12:
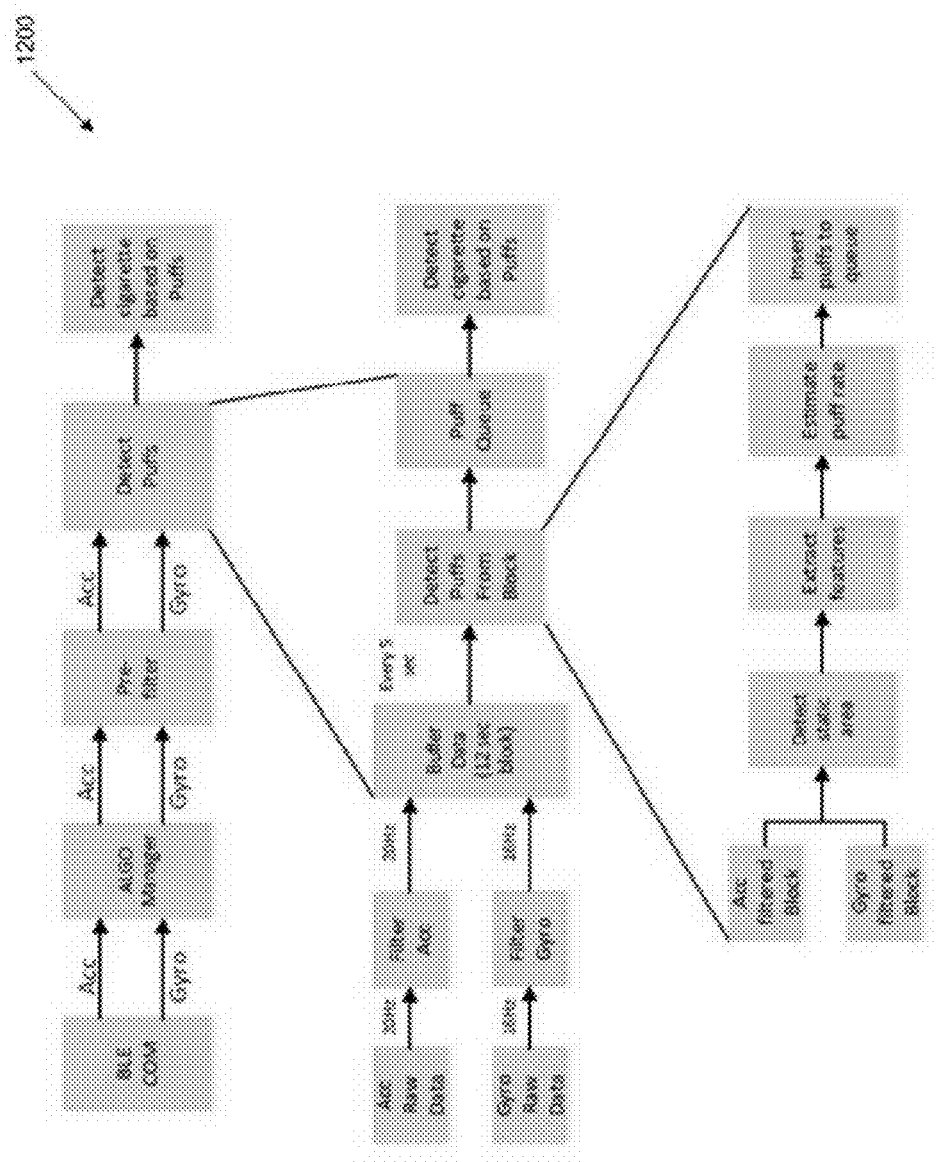
FIG. 12 is a flowchart of a method of detecting a probability of a user smoking a cigarette, in accordance with some further embodiments.

FIG. 12 is a flowchart of a method 1200 of detecting a probability of a user smoking a cigarette, in accordance with some further embodiments.

First, sensor data (e.g., accelerometer data (Acc) and gyroscope data (Gyro)) may be transmitted from a wearable device to the user device, server, and/or gesture analysis engine. The sensor data may be transmitted via one or more wireless or wired communication channels. The wireless communication channels comprise BLE (Bluetooth Low Energy), WiFi, 3G, and/or 4G networks.

As shown in FIG. 12, the sensor data may be transmitted to an algorithm manager (ALGO Manager). The ALGO Manager may be a module located on the wearable device, user device, server, and/or gesture analysis engine. The ALGO Manager may be configured to extract a portion of the sensor data, and transmit the extracted portion to a filter module (Pre-Filter). The Pre-Filter may be located on the wearable device, user device, server, and/or gesture analysis engine. The Pre-Filter may apply a filter to the sensor data prior to the analysis of the sensor data. In some embodiments, analyzing the sensor data may further comprise applying a filter to the sensor data. The filter may be applied to reduce noise in the sensor data. In some embodiments, the filter may be a higher order complex filter such as a finite-impulse-response (FIR) filter or an infinite-impulse-response (IIR) filter. For example, the filter may be a Kalman filter or a Parks-McClellan filter. In some embodiments, the filter may be applied using one or more processors on the wearable device. Alternatively, the filter may be applied using one or more processors on the user device. Optionally, the filter may be applied using one or more processors on the server. In some embodiments, the filter may be applied using one or more processors in the gesture analysis engine.

The filtered sensor data may be provided to the gesture analysis engine as buffered data of a predetermined time block (e.g., in 12 secs block). The buffered data may be received at gesture analysis engine at a predetermined time interval (e.g., every 5 secs). The gesture analysis engine may be configured to detect probabilities of puffs from the buffered blocks. For example, the gesture analysis engine may be configured to detect static areas in candidate puff signals. The static areas may correspond to regions in the signals where one or both signals are beneath predefined respective thresholds. These regions may correspond to 'suspected puff areas'. The gesture analysis engine may be configured to extract features from the candidate puff signals, and to analyze the features using statistics (e.g., multi-dimensional distribution function) to produce a puff rating. The candidate puffs with the respective puff ratings may be inserted into a puff queue. The gesture analysis engine may be configured to determine the probability of the user smoking based on the puffs in the puff queue. Additionally, the method of FIG. 12 may incorporate one or more of steps previously described in FIGS. 10 and 11.

Sensor Data Management

In some embodiments, the sensor data may be stored in a memory on the wearable device when the wearable device is not in operable communication with the user device and/or the server. In those embodiments, the sensor data may be transmitted from the wearable device to the user device when operable communication between the user device and the wearable device is re-established. Alternatively, the sensor data may be transmitted from the wearable device to the server when operable communication between the server and the wearable device is re-established.

In some embodiments, a data compression step may be applied to the sensor data prior to data transmission. The compression of the sensor data can reduce a bandwidth required to transmit the sensor data, and can also reduce a power consumption of the wearable device during transmission of the sensor data. In some embodiments, the data compression step may comprise calculating a difference between samples of the sensor data. The difference may be time-based (t) or spatial-based (X, Y, and Z). For example, if there is no difference in the acceleration magnitudes of a current data sample and previous data samples, the sensor data is not re-transmitted. Conversely, if there is a difference in the acceleration magnitudes of the current data sample and previous data samples, only the difference may be transmitted (e.g., from the wearable device to the user device and/or server). The sensor data may be compressed using a predefined number of bits (e.g., 16 bits). For example, 32-bit or 64-bit sensor data may be compressed to 16 bits.

The sensor data may be collected at a predetermined frequency. In some embodiments, the predetermined frequency may be configured to optimize and/or reduce a power consumption of the wearable device. In some embodiments, the predetermined frequency may range from about 10 Hz to about 20 Hz. In some embodiments, one or more sensors may be configured to collect the sensor data at a first predetermined frequency when the gesture analysis engine determines that the user is not smoking. The one or more sensors may be configured to collect the sensor data at a second predetermined frequency when the gesture analysis engine determines a high probability that the user is smoking. The second predetermined frequency may be higher than the first predetermined frequency. In some embodiments, the one or more sensors may be configured to collect the sensor data for a predetermined time duration. Optionally, the one or more sensors may be configured to collect the sensor data continuously in real-time when the wearable device is powered on.

A frequency of the sensor data collection may be adjusted based on the different times of the day and/or the different geographical locations. For example, the frequency of the sensor data collection may be increased at times of the day and/or at geographical locations where the probability of the user performing the predefined gesture is above a predetermined threshold value. Conversely, the frequency of the sensor data collection may be decreased at times of the day and/or at geographical locations where the probability of the user performing the predefined gesture is below a predetermined threshold value. In some embodiments, one or more sensors in the wearable device and/or the user device may be selectively activated based on the probability of the user performing the predefined gesture at different times of the day and/or at different geographical locations.

In some embodiments, the one or more sensors may comprise a first group of sensors and a second group of sensors. The first and second groups of sensors may be selectively activated to reduce power consumption of the wearable device, and to reduce an amount of the collected sensor data. The reduction in the sensor data can allow faster analysis/processing of the sensor data, and reduce an amount of memory required to store the sensor data.

In some embodiments, the first group of sensors may be activated when the wearable device is powered on. The first group of sensors may be used to determine whether there is a high probability that the user is smoking. The second group of sensors may be inactive prior to determining whether the user is smoking. The second group of sensors may be selectively activated when the wearable device is powered on, depending on whether there is a high probability that the user is smoking. For example, the second group of sensors may be selectively activated upon determining that there is a high probability that the user is smoking. The second group of sensors may be activated to collect additional sensor data, so as to confirm that the user is smoking, monitor the smoking, and collect additional smoking-related data.

In some embodiments, the wearable device may be configured to operate in a plurality of energy and/or performance modes. The modes may comprise a low power mode in which only some of the sensors are turned on. The wearable device may have low power consumption when the wearable device is in the low power mode. An accuracy of detection of the predefined gesture may be reduced when the wearable device is in the low power mode, since less information (less amount of sensor data) is available for analysis in the low power mode. Additionally, the modes may comprise an accuracy mode in which all of the sensors are turned on. The wearable device may have high power consumption when the wearable device is in the accuracy mode. An accuracy of detection of the predefined gesture may be improved when the wearable device is in the accuracy mode, since more information (greater amount of sensor data) is available for analysis in the accuracy mode. In some embodiments, the sensor data may not be analyzed when the wearable device and/or the user device is in an idle mode or a charging mode.

In some embodiments, the sensor data may comprise one or more parameters. The parameters may comprise at least one of the following: (1) a hand which the user smokes with; (2) a pulse pattern of the user; (3) a location of the user; (4) a wearable device identifier and a user device identifier (e.g., MSISDN or Android ID or Advertiser ID or IMEI+mac address); and (5) smoking statistics of the user. The one or more parameters may be unique to the user, the wearable device, and/or the user device. In some embodiments, an identity of the user may be authenticated based on the one or more parameters. The identity of the user may need to be authenticated to prevent misuse of the wearable device and/or user device.

User Interface

In some embodiments, the gesture analysis engine can generate one or more graphical user interfaces (GUIs) comprising statistics of the user's behavior. The GUIs may be rendered on a display screen on a user device. A GUI is a type of interface that allows users to interact with electronic devices through graphical icons and visual indicators such as secondary notation, as opposed to text-based interfaces, typed command labels or text navigation. The actions in a GUI are usually performed through direct manipulation of the graphical elements. In addition to computers, GUIs can be found in hand-held devices such as MP3 players, portable media players, gaming devices and smaller household, office and industry equipment. The GUIs may be provided in a software, a software application, a web browser, etc. The GUIs may be displayed on a user device (e.g., user device 102 of FIG. 1). The GUIs may be provided through a mobile application. Examples of such GUIs are illustrated in FIGS. 13 through 19 and described as follows.

Figure 13:
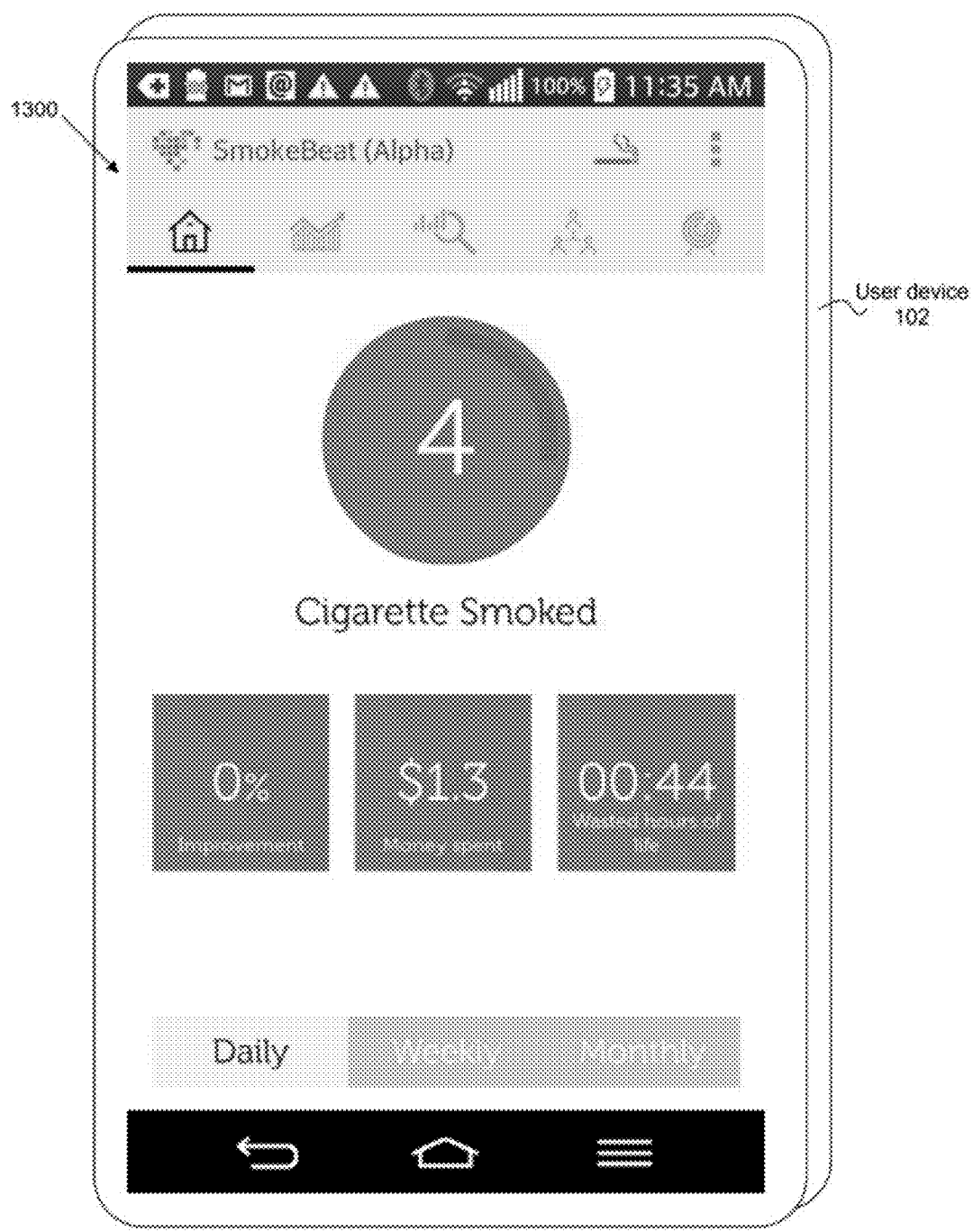
FIG. 13 illustrates an exemplary window depicting the number of cigarettes smoked during a day by a user, in accordance with some embodiments.
Figure 14:
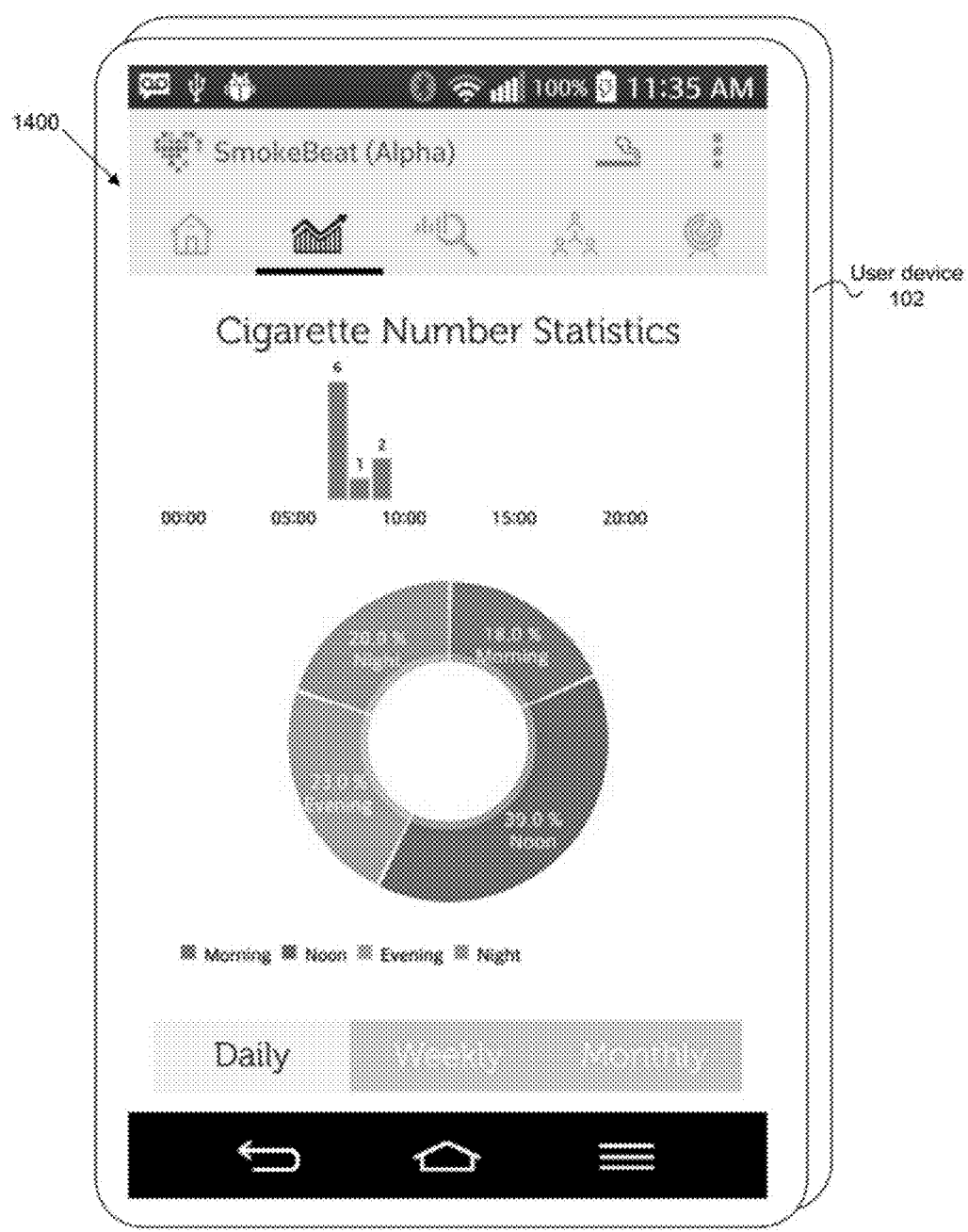
FIG. 14 illustrates an exemplary window depicting the breakdown of cigarettes smoked by time of day, in accordance with some embodiments.
Figure 15:
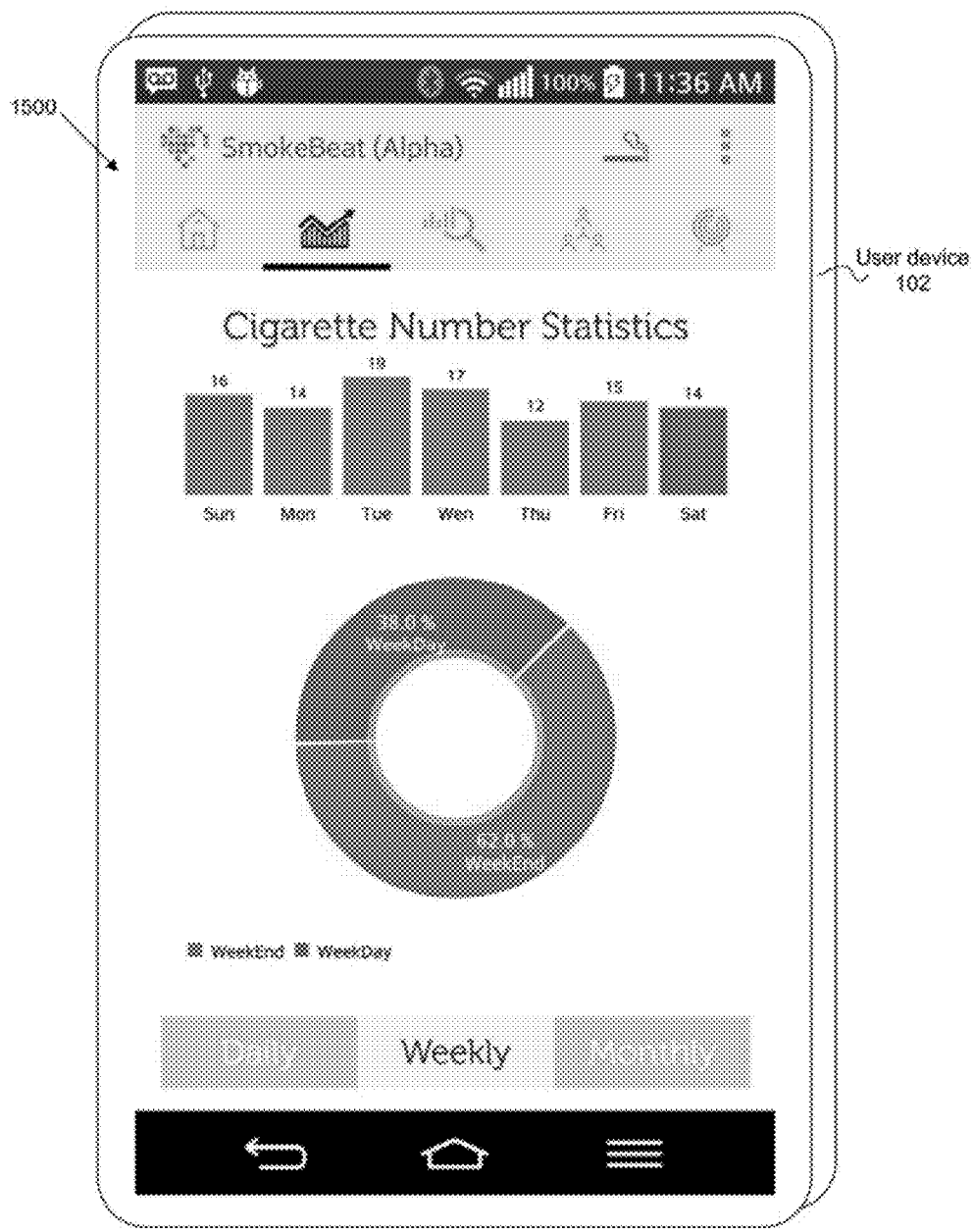
FIG. 15 illustrates an exemplary window depicting the number of cigarettes smoked by a user on weekdays and weekends during a week, in accordance with some embodiments.
Figure 16:
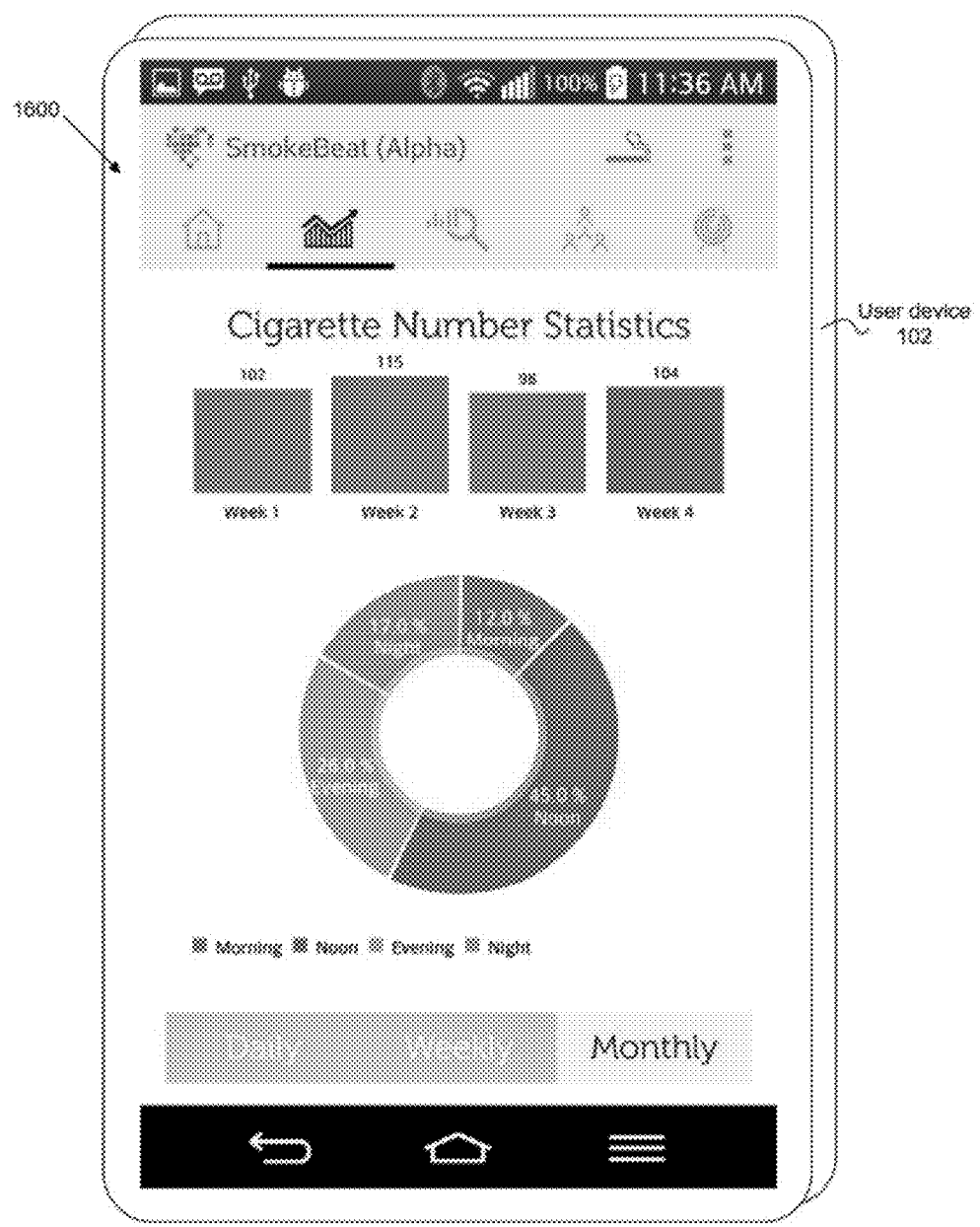
FIG. 16 illustrates an exemplary window depicting the breakdown of cigarettes smoked by time of day over a period of four weeks, in accordance with some embodiments.
Figure 17:
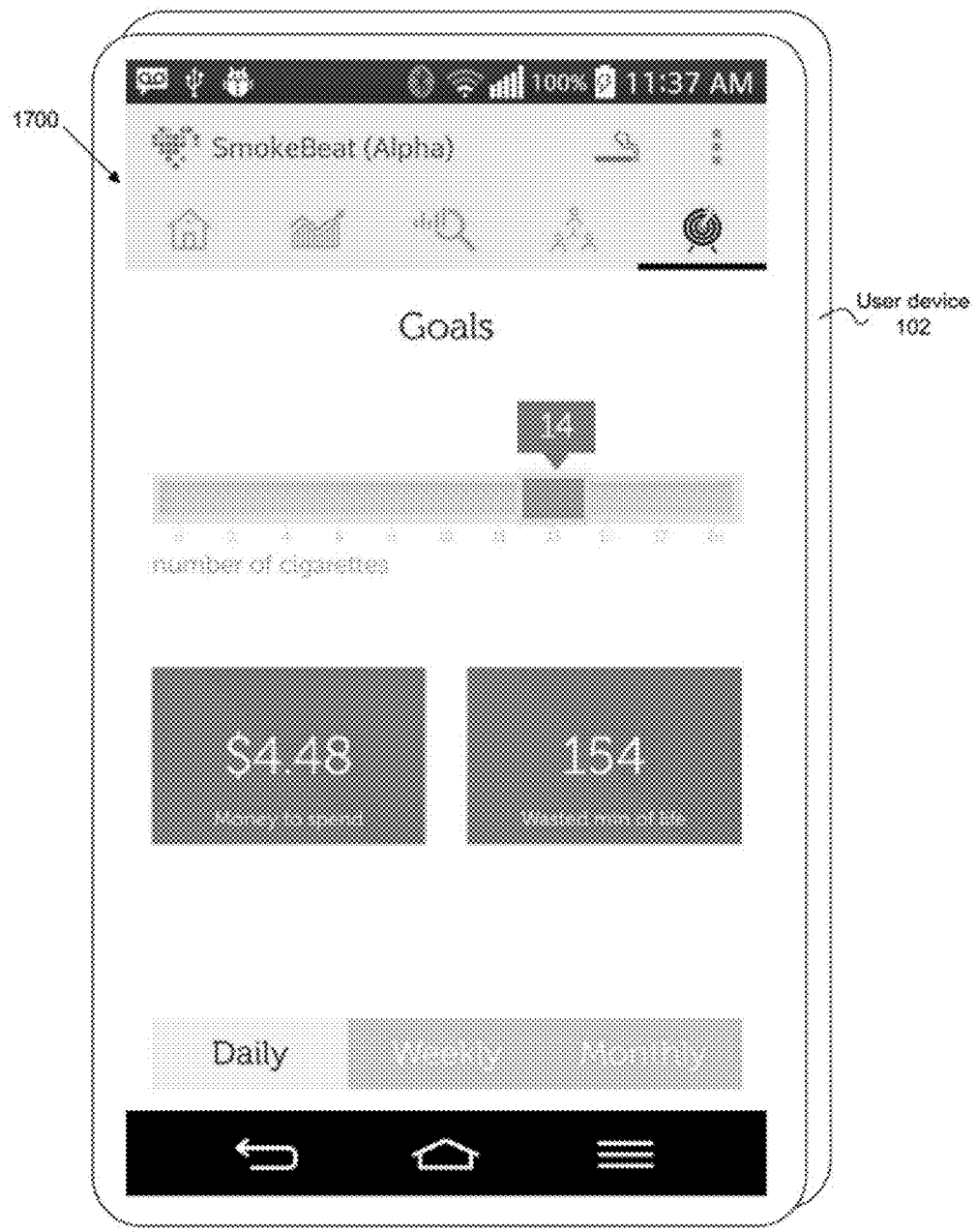
FIG. 17 illustrates an exemplary window depicting a user's daily goal, in accordance with some embodiments.
Figure 18:
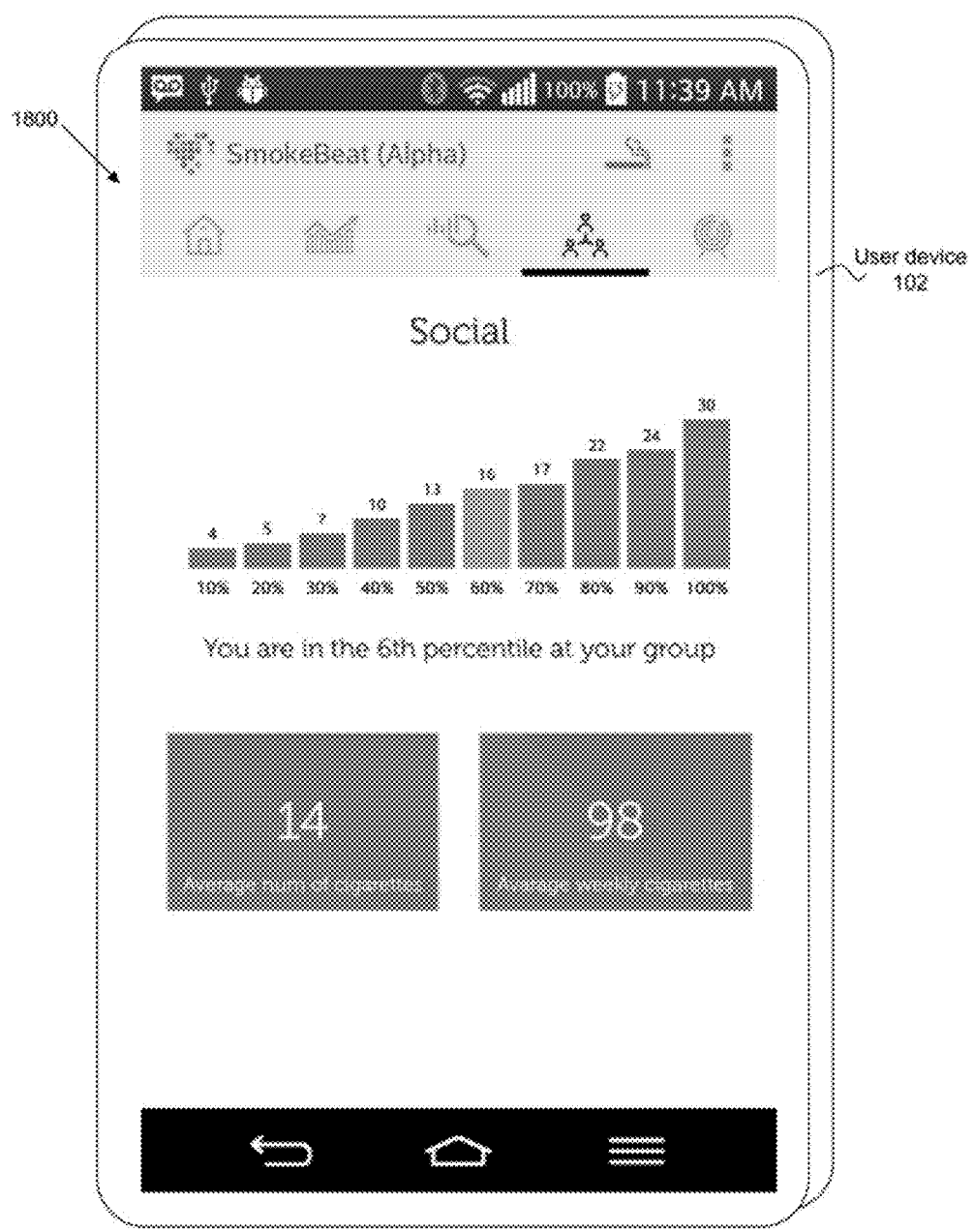
FIG. 18 illustrates an exemplary window ranking a smoker's cessation success/performance against other smokers in a group, in accordance with some embodiments.

Window 1300 of FIG. 13 may be generated after the user device is connected to the gesture analysis engine and data has been obtained from the gesture analysis engine. Window 1300 may be an exemplary window depicting various smoking monitoring metrics. In some cases, window 1300 may correspond to a home landing page that a user will view first when opening the application or logging into the application. Window 1300 may indicate the smoking metrics for the user by day. In the example of FIG. 13, window 1300 may display that the user had smoked 4 cigarettes for that day, with 0% improvement compared to the previous day, spent $1.30 on cigarettes, and potentially 'wasted' 44 minutes of his/her life by smoking the 4 cigarettes that day. The amount of time 'wasted' may be indicative of a health impact from smoking a number of cigarettes.

In some embodiments, a user may view his/her smoking patterns for different times within a day. For example, as shown in window 1400 of FIG. 14, a user may have smoked 9 cigarettes for that day, over three smoking episodes (6+1+2 cigarettes). The piechart in window 1400 further illustrates that out of the total smoking for that day, 18% of the smoking occurred in the morning, 39% occurred at noon, 23% occurred in the evening, and 20% occurred at night.

In some embodiments, a user may view his/her smoking metrics by week. For example, as shown in window 1500, the barchart indicates that the user smoked 16 cigarettes on Sunday, 14 on Monday, 19 on Tuesday, 17 on Wednesday, 12 on Thursday, 15 on Friday, and 14 on Saturday. It may be observed that the user smoked the least on Thursday and smoked the most on Tuesday. The piechart in window 1500 further illustrates that 38% of the smoking occurred on weekdays and 62% occurred on weekends.

In some embodiments, a user may view his/her smoking metrics by month. For example, as shown in window 1600, the barchart indicates that the user smoked 102 cigarettes in Week 1, 115 in Week 2, 98 in Week 3, and 104 in Week 4. It may be observed that the user smoked the least in Week 3 and smoked the most in Week 2. The piechart in window 1600 further illustrates that 12% of the smoking occurred in the morning, 45% occurred at noon, 26% occurred in the evening, and 17% occurred at night.

In some embodiments, a user may set goals in the application. For example, as shown in window 1700 of FIG. 17, the user may set a goal of limiting to 14 cigarettes within a day. This may require the user to spend $4.48 on the cigarettes. Additionally, smoking 14 cigarettes could potentially waste 154 mins of the user's life.

In some embodiments, a user may view his smoking behavior compared to other users. For example, as shown in window 1800 of FIG. 18, smoking an average of 14 cigarettes per day and an average of 98 cigarettes per week may place the user in the $6^{th}$ percentile within the group of users.

Figure 19:
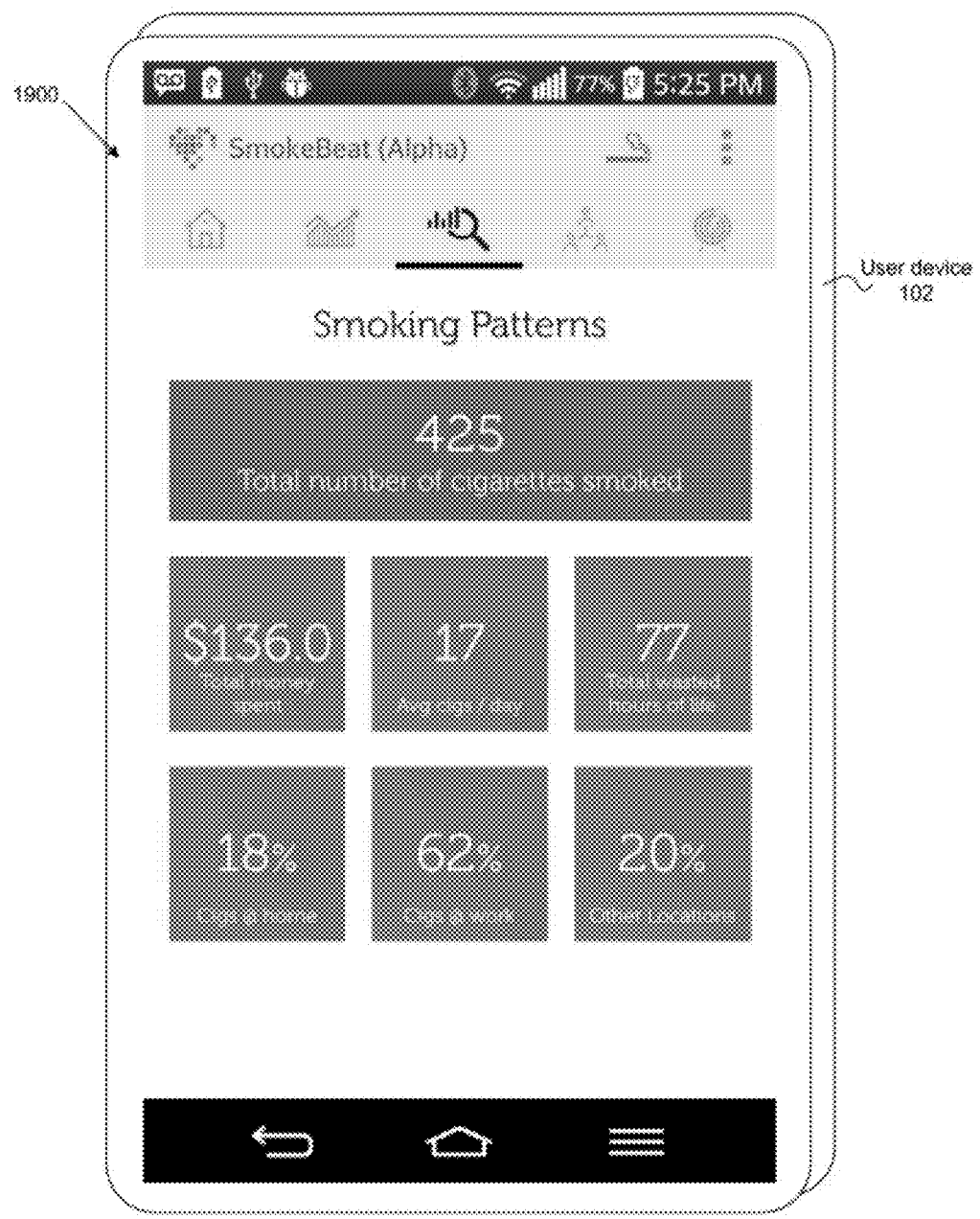
FIG. 19 illustrates an exemplary window showing a plurality of smoking metrics of a user, in accordance with some embodiments.

In some embodiments, a user may view various metrics associated with his smoking patterns. For example, window 1900 of FIG. 19 illustrates that the user had smoked a total of 425 cigarettes, spent $136 on cigarettes, smoked an average of 17 cigarettes per day, and potentially 'wasted' 77 hours of his life by smoking. Additionally, window 1900 shows that 18% of the smoking occurred at home, 62% occurred at work, and 20% occurred at other locations.

In the GUIs of FIGS. 13 to 19, different colors and shading may be used to differentiate the segments from each other. The numbers and words for various metrics may be provided in different colors and shades to improve readability, and to distinguish the metrics from one another. Any color scheme or any other visual differentiation scheme may be contemplated.

In some embodiments, a user may be able to share his smoking metrics information with other users or contacts. The user may also select one or more of social media links in the windows to share the smoking metrics information with other users (e.g., his network of contacts in the selected social media). The social media links may comprise links to social media such as Facebook™ and Twitter™.

In some embodiments, the gesture analysis engine may be configured to receive puffs/cigarettes information from a plurality of wearable devices and/or user devices. Each wearable device and/or user device may serve as a data node that provides user consumption data to a database connected to the gesture analysis engine. The database may be updated in real-time with the user's smoking data. The gesture analysis engine may be configured to generate consumption statistics and determine smoking-related social patterns. For example, the gesture analysis engine can generate a visual representation of aggregated consumption data (e.g., total number of cigarettes smoked by day/week/month). The consumption data may further include the market share of each cigarettes brand, consumption per user gender by cigarette brand, and consumer preferences. Consumer preferences may include time of smoking by cigarette brand, location of smoking (home/work/driving/other), smoking frequency (per event, per time, per person), consumption per capita, and correlation of smoking with consumption of other products (such as coffee). The gesture analysis engine can also analyze the consumption statistics to determine consumption patterns (correlation) for different brands, geography, and/or time periods. In some cases, by having multiple inputs of smoking behavior, the gesture analysis engine may be capable of cross-learning and recognizing the correlation/impact between different smokers, which can help evaluate the optimized paths for smoking cessation for the user as well as his/her social circle. For example, the gesture analysis engine may detect that user X is a leader in his social circle and cessation of smoking by user X may significantly influence others in his social circle to change their smoking behavior. Accordingly, the gesture analysis engine may provide additional incentives to user X to assist him in smoking cessation, so that the effect can be proliferated across the social circle.

In one or more of the previously-described embodiments, the gesture analysis system is capable of differentiating between smoking patterns of the moving hand and other movements that are not smoking related. The algorithms described herein may be based in part on statistical analysis, machine learning, signal processing, pattern recognition, and detection theory. An algorithm may assume a certain smoking model and try to detect the smoking of a cigarette based on the model. The algorithm may also estimate a different smoking model for each smoker and use the model to detect a specific smoker is smoking.

In some embodiments, the gesture analysis system can analyze geographical, time-based and user attributes (e.g., age, gender, job vocation, etc.) cigarette consumption trends by aggregating data from a plurality of wearable devices worn by a plurality of users who smoke.

In some embodiments, the gesture analysis system can be used to implement a smoking cessation program based in part on cognitive behavioral psychology, by using constant monitoring of near real time smoking and goal accomplishment in the program. Using the monitoring system, a user can be notified of each cigarette that he/she smoked, and receive instant notification regarding his/her smoking patterns and information on the progress in reaching his/her smoking reduction goals. Real-time generation of smoking alerts can be highly effective for smoking cessation.

Additionally, by transmitting smoking behavior data to a server for further analysis, various pattern recognition algorithms can be used to determine the required milestone/incentive to be offered to the user in order to effectively influence his/her smoking habits, which can help to change the user's smoking behavior and decrease the health risks caused by smoking.

As used herein A and/or B encompasses one or more of A or B, and combinations thereof such as A and B. It will be understood that although the terms "first," "second," "third" etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A gesture recognition method comprising:
   selectively activating a first sensor out of a sensor group located on a wearable device, wherein said wearable device is configured to be worn by a user, and the sensor group comprises a first sensor and a second sensor;
   obtaining first sensor data collected using the first sensor;
   analyzing the first sensor data to determine a likelihood of the user performing a predefined gesture based on a magnitude of a first motion vector in the first sensor data;
   determining whether the likelihood that the user is performing the predefined gesture is below or above a threshold value;
   selectively activating the second sensor to collect additional sensor data comprising a second motion vector having a magnitude when the likelihood that the user is performing the predefined gesture is above the threshold value; and
   comparing the magnitudes of the first and second motion vectors in the collected sensor data without requiring comparing of the first and second motion vectors to a plurality of physical motion profiles, to determine whether the user is performing the predefined gesture.

2. The method of claim 1, wherein the analyzing of the sensor data is carried out with aid of one or more processors onboard the wearable device.

3. The method of claim 1, wherein the analyzing of the sensor data is carried out with aid of one or more processors onboard a user device or a remote server in communication with the wearable device, wherein the user device and the remote server are provided separate from the wearable device.

4. The method of claim 1, wherein the predefined gesture is selected from a group of different gestures associated with different activities including the user smoking or about to smoke a cigarette, eating, drinking, or taking medication.

5. The method of claim 1, where the sensor group comprises an accelerometer and a gyroscope, wherein the magnitudes of the two or more motion vectors comprise: (1) a magnitude of an acceleration vector obtained from the accelerometer, and (2) a magnitude of an angular velocity vector obtained from the gyroscope.

6. The method of claim 5, further comprising: determining the likelihood of the user performing the predefined gesture by comparing the magnitudes of the acceleration vector and the angular velocity vector.

7. The method of claim 5, further comprising: calculating a pitch angle, roll angle, and/or yaw angle of the wearable device based on at least the acceleration vector or the angular velocity vector, and determining the likelihood of the user performing the predefined gesture based on the calculated angle(s).

8. The method of claim 1, wherein the sensor group comprises one or more of the following: a magnetometer, a heart rate monitor, a global positioning system (GPS) receiver, a barometer, an external temperature sensor, a microphone, a skin temperature sensor, a capacitive sensor, or a sensor configured to detect a galvanic skin response.

9. The method of claim 1, wherein the analyzing of the sensor data comprises calculating a multi-dimensional distribution function, wherein said multi-dimensional distribution function comprises a plurality of features associated with various aspects of the predefined gesture, and wherein the plurality of features are extracted from the sensor data and de-correlated using Singular Value Decomposition (SVD).

10. The method of claim 1, further comprising: applying a data compression step to the sensor data, wherein the data compression step is configured to at least reduce a bandwidth required to transmit the sensor data or reduce a power consumption of the wearable device during the transmission of the sensor data.

11. The method of claim 10, wherein the sensor group comprises a plurality of sensors configured to collect the sensor data at a plurality of different frequencies, wherein the data compression step is used to extract a portion of the sensor data when at least one of the plurality of sensors is collecting the sensor data above a certain frequency, and wherein the extracted portion of the sensor data is analyzed to determine the likelihood of the user performing the predefined gesture.

12. The method of claim 1, wherein the second sensor is inactive when the likelihood that the user is performing the predefined gesture is below the threshold value, and wherein the second sensor is selectively activated (1) when the wearable device is powered on and the likelihood that the user is performing the predefined gesture is above the threshold value, or (2) upon determining that the user is performing the predefined gesture.

13. The method of claim 1, wherein the wearable device is configured to operate in a plurality of modes comprising a low power mode and an accuracy mode, and wherein an accuracy of detecting whether the user is performing the predefined gesture is improved when the wearable device is in the accuracy mode compared to the low power mode.

14. A gesture recognition method comprising:
obtaining sensor data collected using at least one sensor located on a wearable device, wherein said wearable device is configured to be worn by a user;
analyzing the sensor data by comparing magnitudes of two or more motion vectors in the sensor data without requiring comparing of the motion vectors to a plurality of physical motion profiles, to determine a likelihood of the user performing a predefined gesture; and
determining whether the likelihood that the user is performing the predefined gesture is below or above a threshold value,
wherein the at least one sensor (1) starts collecting additional sensor data at a first predetermined frequency when the likelihood that the user is performing the predefined gesture is below the threshold value, or (2) starts collecting additional sensor data at a second predetermined frequency different from the first predetermined frequency when the likelihood that the user is performing the predefined gesture is above the threshold value.

15. A system for implementing gesture recognition, comprising:
a memory for storing sensor data collected using a sensor group located on a wearable device, wherein said wearable device is configured to be worn by a user, and the sensor group comprises a first sensor and a second sensor; and
one or more processors configured to:
selectively activate the first sensor;
obtain first sensor data collected using the first sensor;
analyze the first sensor data to determine a likelihood of the user performing a predefined gesture based on a magnitude of a first motion vector in the first sensor data;
determine whether the likelihood that the user is performing the predefined gesture is below or above a threshold value;
selectively activate the second sensor to collect additional sensor data comprising a second motion vector having a magnitude when the likelihood that the user is performing the predefined gesture is above the threshold value; and
compare the magnitudes of the first and second motion vectors in the collected sensor data without requiring comparing of the first and second motion vectors to a plurality of physical motion profiles, to determine whether the user is performing the predefined gesture.

16. The system of claim 15, wherein the one or more processors are located onboard the wearable device.

17. The system of claim 15, wherein the one or more processors are located onboard a user device or a remote server in communication with the wearable device, wherein the user device and the remote server are provided separate from the wearable device.

18. The system of claim 15, wherein the predefined gesture is selected from a group of different gestures associated with different activities including the user smoking or about to smoke a cigarette, eating, drinking, or taking medication.

19. The system of claim 15, where the sensor group comprises an accelerometer and a gyroscope, wherein the magnitudes of the two or more motion vectors comprise: (1) a magnitude of an acceleration vector obtained from the accelerometer, and (2) a magnitude of an angular velocity vector obtained from the gyroscope.

20. The system of claim 19, where the one or more processors are configured to determine the likelihood of the user performing the predefined gesture by comparing the magnitudes of the acceleration vector and the angular velocity vector.

21. The system of claim 19, where the one or more processors are configured to calculate a pitch angle, roll angle, and/or yaw angle of the wearable device based on at least the acceleration vector or the angular velocity vector, and determine the likelihood of the user performing the predefined gesture based on the calculated angle(s).

22. The system of claim 15, wherein the sensor group comprises one or more of the following: a magnetometer, a heart rate monitor, a global positioning system (GPS) receiver, a barometer, an external temperature sensor, a microphone, a skin temperature sensor, a capacitive sensor, or a sensor configured to detect a galvanic skin response.

23. The system of claim 15, wherein the one or more processors are configured to analyze the sensor data by calculating a multi-dimensional distribution function, wherein said multi-dimensional distribution function comprises a plurality of features associated with various aspects of the predefined gesture, and wherein the plurality of features are extracted from the sensor data and de-correlated using Singular Value Decomposition (SVD).

24. The system of claim 15, wherein the one or more processors are configured to apply a data compression step to the sensor data, wherein the data compression step is configured to at least reduce a bandwidth required to transmit the sensor data or reduce a power consumption of the wearable device during the transmission of the sensor data.

25. The system of claim 17, wherein the sensor group comprises a plurality of sensors configured to collect the sensor data at a plurality of different frequencies, wherein the data compression step is used to extract a portion of the sensor data when at least one of the plurality of sensors is collecting the sensor data above a certain frequency, and wherein the one or more processors are configured to analyze the extracted portion of the sensor data to determine the likelihood of the user performing the predefined gesture.

26. The system of claim 15, wherein the second sensor is inactive when the likelihood that the user is performing the predefined gesture is below the threshold value, wherein the one or more processors are configured to selectively activate the second sensor (1) when the wearable device is powered on and the likelihood that the user is performing the predefined gesture is above the threshold value, or (2) upon determining that the user is performing the predefined gesture.

27. The system of claim 15, wherein the wearable device is configured to operate in a plurality of modes comprising a low power mode and an accuracy mode, and wherein an accuracy of detecting whether the user is performing the predefined gesture is improved when the wearable device is in the accuracy mode compared to the low power mode.

28. A system for implementing gesture recognition, comprising:
    a memory for storing sensor data collected using at least one sensor located on a wearable device, wherein said wearable device is configured to be worn by a user; and
    one or more processors configured to:
        analyze the sensor data by comparing magnitudes of two or more motion vectors in the sensor data, without comparing of the motion vectors to a plurality of physical motion profiles, to determine a likelihood of the user performing a predefined gesture; and
        determine whether the likelihood that the user is performing the predefined gesture is below or above a threshold value,
    wherein the at least one (1) starts collecting additional sensor data at a first predetermined frequency when the likelihood that the user is performing the predefined gesture is below the threshold value, or (2) starts collecting additional sensor data at a second predetermined frequency different from the first predetermined frequency when the likelihood that the user is performing the predefined gesture is above the threshold value.

* * * * *